(12) United States Patent
Fischetti et al.

(10) Patent No.: US 6,737,521 B1
(45) Date of Patent: *May 18, 2004

(54) DELIVERY AND EXPRESSION OF A HYBRID SURFACE PROTEIN ON THE SURFACE OF GRAM POSITIVE BACTERIA

(75) Inventors: Vincent A. Fischetti, West Hempstead, NY (US); Gianni Pozzi, Siena (IT); Olaf Schneewind, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/302,756

(22) PCT Filed: Mar. 12, 1993

(86) PCT No.: PCT/US93/02355

§ 371 (c)(1),
(2), (4) Date: Mar. 7, 1995

(87) PCT Pub. No.: WO93/18163

PCT Pub. Date: Sep. 16, 1993

Related U.S. Application Data

(63) Continuation-in-part of application No. 07/851,082, filed on Mar. 13, 1992, now abandoned, which is a continuation-in-part of application No. 07/814,323, filed on Dec. 31, 1991, now abandoned, which is a continuation of application No. 07/742,199, filed on Aug. 5, 1991, now abandoned, which is a continuation of application No. 07/522,440, filed on May 11, 1990, now abandoned.

(51) Int. Cl.[7] .......................... C07H 21/04; A61K 39/00; A61K 39/09; C12N 1/20
(52) U.S. Cl. ................ 536/23.4; 424/192.1; 424/200.1; 424/184.1; 424/244.1; 536/23.7; 435/172.3; 435/252.3; 435/253.4; 435/320.1; 935/27.47; 935/72
(58) Field of Search .......................... 424/192.1, 200.1, 424/244.1, 184.1; 435/172.3, 252.3, 253.4, 320.1; 536/23.4, 23.7; 835/27.47, 72

(56) References Cited

U.S. PATENT DOCUMENTS

| | | | |
|---|---|---|---|
| 4,722,840 A | * | 2/1988 | Valenzuela et al. |
| 4,859,465 A | * | 8/1989 | Rutter |
| 5,124,153 A | * | 6/1992 | Beachey et al. |
| 5,149,532 A | * | 9/1992 | Brunnel |
| 5,500,353 A | * | 3/1996 | Smit et al. |
| 5,616,686 A | * | 4/1997 | Fischetti et al. |
| 5,707,822 A | * | 1/1998 | Fischetti et al. |
| 5,733,540 A | * | 3/1998 | Lee |
| 5,786,205 A | * | 7/1998 | Fischetti et al. |
| 5,792,463 A | * | 8/1998 | Valenzuela et al. |
| 5,820,860 A | * | 10/1998 | Michel et al. |
| 5,821,088 A | * | 10/1998 | Darzins et al. |
| 5,843,444 A | * | 12/1998 | Michel et al. |
| 5,847,081 A | * | 12/1998 | Michel et al. |
| 5,858,362 A | * | 1/1999 | Michel et al. |
| 5,965,390 A | * | 10/1999 | Björck et al. |
| 5,968,521 A | * | 10/1999 | Michel et al. |
| 5,968,763 A | * | 10/1999 | Fischetti et al. |
| 6,063,386 A | * | 5/2000 | Dale et al. |
| 6,419,932 B1 | * | 7/2002 | Dale |

FOREIGN PATENT DOCUMENTS

| | | | |
|---|---|---|---|
| EP | 0371199 | * | 6/1990 |
| EP | 0406857 | * | 1/1991 |
| EP | 0532090 | * | 3/1993 |
| WO | 8909064 | * | 10/1989 |
| WO | 9015872 | | 12/1990 |
| WO | 9220805 | * | 11/1992 |

OTHER PUBLICATIONS

Bessen et al, In: New Perspectives on Streptococcal Infections Zbl. Bakt. Suppl. 22 pp. 200–202, 1992.*
Hollingshead et al, Infection & Immunity. 55/12: 3237–3239, Dec. 1987.*
Pozzi et al, J. Bacterial. 170/4: 1969–1972, Apr. 1988.*
Hruby et al PNAS 88:3190–3194, Apr. 1991.*
Bessen et al, J. of Immunology 145/4: 1251–1256, Aug. 1990.*
Pozzi et al, J of Bacteriol. 161/3:909–912, Mar. 1985.*
Haynes 1993 Science, 260: 1279–1286.*
Fox 1994, Bio/Technology 12 pp128.*
Hoffman et al 1987, Science, 237:639–642.*
Cox 1991, TIBTECH, vol 9:389–394.*
Hoffman et al 1993 Mol.Immunological Consideration . . . Ed. Good et al pp 149–167.*
Charoenvit et al 1991, Science, 251:668–671.*
Dougan et al 1989, J. Gen Microbiol 135:1397–1406.*
Pan et al, 1995, Nature Medicine 1(5):471–477.*
Schödel et al 1991, Gene 99:255–259.*
Schneewind et al, 1993. The EMBO Journal, 12(12):4803–811.*
Oggioni et al, 1995, Vaccine, 13(8):775–779.*
Homonylo–McGavin et al, 1996, J. Bacteriology, 178(3):801–07.*
Pozzi et al, 1994, Vaccine, 12(12):1071–1077.*
Navarre et al, 1996, J. Bacteriology, 178(2):441–46.*
Oggioni et al, 1996, Gene, 169:85–90.*
Fischetti et al 1990, Mol. Microbiol. 4(9):1603–1605.*
Ikonomidis et al 1995. Vaccines 95. pp 317–326.*
Greenwood et al, 1991, J. Mol. Biol. 220(4):821–827.*
Fischetti, 1991, ScientificAmerican; Jun. 1991, 58–65.*
Uhlen et al. 1983. Gene fusion vectors based on the gene for Streptococcal protein A. GENE 23: 369–378.*
Poirier et al. 1989. Fibrinogen binding and resistance to phagocytosis of STreptococcus sanguis expressing cloned M protein of S. Pyogenes. Infection and Immunity 57(1):29–35.*

(List continued on next page.)

Primary Examiner—Nita Minnifield
(74) Attorney, Agent, or Firm—Burns, Doane, Swecker & Mathis, LLP

(57) ABSTRACT

Process is described for the delivery and expression of hybrid surface proteins to the surface of bacteria. The transformed bacteria are useful as vaccines, for the delivery of other active peptides to animal hosts, as diagnostic reagents and for other purposes.

47 Claims, 14 Drawing Sheets

OTHER PUBLICATIONS

Fischetti. 1989. Sterptococcal M protein: Molecular design and biological behavior. Clin. Microbiol. Rev. 2(3):285–314.*

Charbit et al. 1987. Presentation of two epitopes of the preS2 region of hepatitis B virus on live recombinant bacteria. J. Immunology 139:1658–1664.*

Newton et al. 1991. Expression and immunogenicity of a Sterptococcal M protein epitope inserted in *Salmonella flagellin*. Infection and Immunity. 59(6):2158–2165.*

Wu et al. 1989. Expression of immunogenic epitopes of hepatitis B surface antigen with hybrid flagellin proteins by a vaccine strain of Salmonella. PNAS USA 86:4726–4730.*

Hollingshead et al. 1986. Complete nucleotide sequence of Type6 M protein of the group A streptococcus. J. Biological Chem. 261(4):1677–1686.*

Horinouchi et al. 1982. Nucleotide sequence and functional map of pE194, a plasmid that specifies inducible resistance to macrolide, lincosamide and streptogramin type B antibiotics. J. Bacteriology 150(2):804–814.*

Schwarz et al. 1985. Structure and transcription of human papillomavirus sequences in cervical carcinoma cells. Nature 314:111–114.*

Dyson et al. 1989. The human papillomavirus–16 E7 oncoprotein is able to bind to the retinoblastoma gene product. Science 243:934–936.*

Jochmus–Kudielka. 1989. Antibodies against the human papillomavirus type 16 early proteins in human sera: correlation of anti–E7 reactivity with cervical cancer. J. Natl. Cancer Inst. 81(22):1698–1703.*

Meneguzzi et al. 1991. Immunization against human papillomavirus type 16 tumor cells with recombinant vaccinia viruses expressing E6 and E7. Virology 181:62–69.*

Fischetti et al. Current Opinion in Biotechnology 4:603–610, 1993.*

Medaglini et al PNAS, 92:6868–6872, Jul. 1995.*

Pozzi et al. Infect & Immun. 60(5):1902–1907, May 1992.*

Oggioni et al. Ed. Balla et al. In: DNA Transfer Gene Expression Microorganism. Proc. Eur. pp. 235–240, 1993.*

Harrison et al. Res. Microbiol. 141(7–8): 1009–1012, 1990.*

O'Callaghan et al. Res. Microbiol. 141(7–8):963–969, 1990.*

Pozzi et al. Res. Microbiol. 143(5):449–57, 1992.*

Jagusztyn–Krynicka et al, Inf. & Immunity. 61(3): 1004–1015, 1993.*

Fischetti et al, Science 244(4911):1487–1490, 1989.*

International Journal of Medical Microbiology, 1992, Gustav Fischer Verlag, "New Perspectives on Streptococci and Streptococcal Infections" p. 350–352.

Bio/Technology, vol. 9, No. 12, Dec. 1991, Nature America, Inc., P. Fuchs et al., "Targeting Recombinant Antibodies to the Surface of *Escherichia coli*: Fusion to a Peptidoglycan Associated Lipoprotein", pp. 1369–1372.

Gene, vol. 104, No. 2, Aug. 15, 1991, F. Breitling et al., "A Surface Expression Vector for Antibody Screening", pp. 147–153.

Science, vol. 244, Apr. 7, 1989, AAAS, S.M.C. Newton et al., "Immune Response to Cholera Toxin Epitope Inserted in *Salmonella flagellin*", pp. 70–72.

Nature, vol. 351, Jun. 6, 1991, C.K. Stover et al., "New Use of BCG for Recombinant Vaccines", pp. 456–460.

Infection and Immunity, vol. 60, No. 5, May 1992, G. Pozzi et al., "Delivery and Expression of a Heterologous Antigen on the Surface of Streptococci", pp. 1902–1907.

* cited by examiner

```
  1    Arg Val Phe Pro Arg Gly Thr
       Val Glu Asn Prn
        a   b   c   d   e   f   g
 12        Asp Lys Ala Arg Glu Leu
 18    Leu Asn Lys Tyr Asp Val Glu
 25    Asn Ser Met Leu Gln Ala Asn
 32    Asn Asp Lys Leu Thr Thr Glu
 39    Asn Asn Asn Leu Thr Asp Gln
 46    Asn Lys Asn Leu Thr Thr Glu
 53    Asn Lys Asn Leu Thr Asp Gln
 60    Asn Lys Asn Leu Thr Thr Glu
 67    Asn Lys Asn Leu Thr Asp Gln
 74    Asn Lys Asn Leu Thr Thr Glu
 81    Asn Lys Glu Leu Lys Ala Glu
 88    Glu Asn Arg Leu Thr Thr Glu
 95    Asn Lys Gly Leu Thr Lys Lys
102    Leu Ser Glu Ala Glu Glu Glu
109    Ala
110    Ala Asn Lys Glu Arg Glu Asn
117    Lys Glu Ala Ile Gly Thr Leu
124    Lys Lys Thr Leu Asp Glu Thr
131                Val Lys Asp Lys
135    Ile Ala Lys Glu Gln Glu Ser
142    Lys Glu Thr Ile Gly Thr Leu
149    Lys Lys Thr Leu Asp Glu Thr
156                Val Lys Asp Lys
160    Ile Ala Lys Glu Gln Glu Ser
167    Lys Glu Thr Ile Gly Thr Leu
174    Lys Lys Thr Leu Asp Glu Thr
181                Val Lys Asp Lys
185    Ile Ala Lys Glu Gln Glu Ser
192    Lys Glu Thr Ile Gly Thr Leu
199    Lys Lys Ile Leu Asp Glu Thr
206                Val Lys Asp Lys
210    Ile Ala Arg Glu Gln Lys Ser
217    Lys Gln Asp Ile Gly Ala Leu
224    Lys Gln Glu Leu Ala Lys Lys
231                    Asp Glu Gly
234    Asn Lys Val Ser Glu Ala Ser
241    Arg Lys Gly Leu Arg Arg Asp
248    Leu Asp Ala Ser Arg Glu Ala
255    Lys Lys Gln Val Glu Lys Asp
```

DELIVERY AND EXPRESSION OF A HYBRID SURFACE PROTEIN ON THE SURFACE OF GRAM POSITIVE BACTERIA

RELATED APPLICATIONS

The present application is a 371 of PCT/US93/02355, filed Mar. 12, 1993; and a continuation-in-part of U.S. application Ser. No. 07/851,082, filed Mar. 13, 1992, now abandoned, which is a continuation-in-part of U.S. application Ser. No. 07/814,323, filed Dec. 31, 1991, now abandoned, which is a continuation of U.S. application Ser. No. 07/742,199, filed Aug. 5, 1991, now abandoned, which is a continuation of U.S. application Ser. No. 07/522,440, filed May 11, 1990, now abandoned.

FIELD OF THE INVENTION

This invention relates generally to products and processes useful to deliver proteins, including protein antigens, to the surface of gram-positive bacteria and firmly attach them to the cell. More specifically, it relates to the production of a fusion protein containing at least the anchor region of the cell associated region of a gram-positive surface protein and any protein, peptide or polypeptide that may be usefully administered to an animal host. The products of the invention which comprise proteins, peptides or polypeptides, as further discussed below, placed on the surface of a gram positive bacteria may be used to deliver such materials to the animal host to elicit an immungenic response, for example the production of protective antibodies or for another useful purpose. The protein, peptide or polypeptide may, for example, be an enzyme or other functional protein necessary for a specific purpose. It may be an antigenic determinant from a bacteria, virus, parasite or fungus. It may be a surface antigen from a mammalian tumor cell or of male sperm. It may be an allergen such as a vespid venom. The invention also relates to novel plasmids, genes, chromosomes and transformed bacteria employed in the production of such fusion proteins. The invention, additionally, provides novel vaccines which employ gram-positive bacteria designed to deliver to an animal host a foreign antigen normally present on a pathogenic microorganism which is associated with the virulence of that pathogen and which will elicit antigens to protect the host against infection or disease caused by the pathogenic microorganism.

The products of the invention are also useful as diagnostic agents.

The invention also provides a means to deliver enzymes, placed on the bacterial surface, to specific areas of interest.

The term "animal" as used herein refers to living beings including mammals such as man; bovines, especially beef cattle; sheep and goats; poultry, especially chickens, ducks and turkeys; as well as fish, especially those raised in fish farms such as salmon, trout and catfish. This invention is of special importance to mammals.

BACKGROUND OF THE INVENTION

The essence of this invention is that it provides a method for the production of novel non-pathogenic gram positive bacteria expressing a hybrid surface protein which may be a hybrid surface antigen, comprising two principal parts, an anchor segment comprised of amino acid residues and an N-terminal active polypeptide segment, both of which will be defined and discussed in more detail below.

This invention will be better understood by consideration of the M protein and its structure. The M protein is a coiled coil surface antigen which is the virulence factor of group A streptococci, a gram positive bacteria. The M protein of *Streptococcus pyogenes* of M type 6 contains 441 amino acid residues.

Its structure will be discussed in more detail below, but it will be useful to discuss the cell associated region at this point. Using the standard one letter representation of amino acids, the structure of the anchor region of the cell associated region of the M6 protein from amino acid residue 407 to residue 441 may be represented as:

LPSTGETANPFFTAAALTVMATAGVAAVVKRKEEN (SEQ ID NO:1)

Reading from the first leucine residue (L) at the N-terminal of the anchor region, the region includes the LPSTGE segment (SEQ ID NO:36); a spacer segment containing three amino acid residues TAN (SEQ ID NO:60); a hydrophobic segment of twenty amino acids, PFTAAALTVMAT-AGVAVV (SEQ ID NO:2); followed by a highly charged tail segment, KRKEEN (SEQ ID NO:61).

It has been observed as a result of structural studies of a large number of surface proteins of gram positive bacteria that the above described anchor region of the M6 protein is highly conserved among all known surface proteins of gram positive bacteria. Many of them are shown by Fischetti et al (Reference 1). Generally, the hydrophobic segment contains about 15 to 20 amino acid residues, the charged tail segment about 4 to 6 amino acid residues, and the spacer segment from about 3 to 6 amino acid residues. Most remarkable however, is the high degree of homology, practically 100% in the LPSTGE (SEQ ID NO:36) segment of the known surface proteins. The variations that occur are almost exclusively at the 3 and 6 positions. Therefore, the region may be generally represented as LPXTGX (SEQ ID NO:37).

The following Table 1 shows the remarkable extent of this homology thus far established amongst forty different surface proteins of gram positive bacteria.

TABLE 1

[SEQ ID NOS: 36, 38–55, AND 59]
SEQUENCED SURFACE PROTEINS FROM
GRAM-POSITIVE BACTERIA

| NAME/ GENE | SURFACE PROTEIN | ORGANISM | LPSTGE | REF | SEQ ID NO. |
|---|---|---|---|---|---|
| 1. M6 | M protein | S. pyogenes | LPSTGE | (2) | 36 |
| 2. M5 | M protein | S. pyogenes | LPSTGE | (3) | 36 |
| 3. M12 | M protein | S. pyogenes | LPSTGE | (4) | 36 |
| 4. M24 | M protein | S. pyogenes | LPSTGE | (5) | 36 |
| 5. M49 | M protein | S. pyogenes | LPSTGE | (6) | 36 |
| 6. M57 | M protein | S. pyogenes | LPSTGE | (7) | 36 |
| 7. M2 | M protein | S. pyogenes | LPSTGE | (8) | 36 |
| 8. ARP2 | IgA binding protein | S. pyogenes | LPSTGE | (8) | 36 |
| 9. ARP4 | IgA binding protein | S. pyogenes | LPSTGE | (9) | 36 |
| 10. FcRA | Fc binding protein | S. pyogenes | LPSTGE | (10) | 36 |
| 11. Prot H | Human IgG Fc binding | S. pyogenes | LPSTGE | (11) | 36 |
| 12. SCP | C5a peptidase | S. pyogenes | LPTTND | (12) | 38 |
| 13. T6 | Protease resistant protein | S. pyogenes | LPSTGS | (13) | 39 |
| 14. bac | IgA binding protein | Gr. B strep | LPYTGV | (14) | 40 |
| 15. Prot G | IgG binding protein | Gr. G strep | LPTTGE | (15) | 41 |
| 16. PAc | Surface protein | S. mutans | LPNTGE | (16) | 42 |
| 17. spaP | Surface protein | S. mutans | LPNTGE | (17) | 42 |

TABLE 1-continued

[SEQ ID NOS: 36, 38–55, AND 59]
SEQUENCED SURFACE PROTEINS FROM
GRAM-POSITIVE BACTERIA

| NAME/ GENE | SURFACE PROTEIN | ORGANISM | LPSTGE | REF | SEQ ID NO. |
|---|---|---|---|---|---|
| 18. spaA | Surface protein | S. sobrinus | LPATGD | (18) | 43 |
| 19. wapA | Wall-associated protein A | S. mutans | LPSTGE | (19) | 36 |
| 20. Sec10 | Surface protein | E. fecalis | LPQTGE | (20) | 44 |
| 21. Asc10 | Surface protein | E. fecalis | LPKTGE | (20) | 59 |
| 22. asa1 | Aggregation substance | E. fecalis | LPQTGE | (21) | 44 |
| 23. Prot A | IgG binding protein | S. aureus | LPETGV | (22) | 45 |
| 24. FnBP | Fibronectin binding protein | S. aureus | LPETGG | (23) | 46 |
| 25. wg2 | Cell wall protease | S. cremoris | LPKTGE | (24) | 59 |
| 26. In1A | Internalization protein | L. monocytogenes | LPTTGE | (25) | 47 |
| 27. Fimbriae | Type 1 fimbriae | A. viscosis | LPLTGA | (26) | 48 |
| 28. Fimbriae | Type 2 fimbriae | A. naeslundii | LPLTGA | (27) | 48 |
| 29. Mrp4 | IgG/Fibrinogen binding | S. pyogenes | LPSTGE | (10) | 36 |
| 30. sof22 | Serum opacity factor | S. pyogenes | LPASGD | (54) | 49 |
| 31. Sfb | Fibronectin binding | S. pyogenes | LPATGD | (55) | 43 |
| 32. Prot L | Light chain binding | P. magnus | LPKAGS | (56) | 50 |
| 33. bca | alpha antigen | Gr. B strep | LPATGE | (57) | 51 |
| 34. fnbA | Fibronectin binding | S. dysgalactiae | LPQTGT | (58) | 52 |
| 35. fnbB | Fibronectin binding | S. dysgalactiae | LPAAGE | (59) | 53 |
| 36. EmmG1 | Mprotein | Gr. G Strep | LPSTGE | (60) | 36 |
| 37. DG12 | Albumin binding protein | Gr. G strep | LPSTGE | (61) | 36 |
| 38. MRP | Surface protein | S. suis | LPNTGE | (62) | 44 |
| 39. FnBp | Fibronectin binding protein | S.aureus | LPETGG | (63) | 54 |
| 40. cna | Collagen binding protein | S. aureus | LPKTGM | (64) | 55 |

It is apparent that this highly homologous region of the surface proteins of gram-positive bacteria is essential to anchoring bacterial surface proteins to the cell (28). This segment, which is referred to herein as the LPXTGX segment (SEQ ID NO: 37), is the crucial segment of the cell associated region of surface protein for anchoring the proteins to the surface of gram positive bacteria.

This discovery has been confirmed by Schneewind et al (65). Using the Protein A molecule of Staphylococcus aureus, these investigators have established that the complete complex (LPXTGX motif (SEQ ID NO:37), hydrophobic domain and charged tail) are necessary to deliver the Protein A molecule to the cell surface and that changes in the LPXTGX motif (SEQ ID NO:37) or deletion thereof will not inhibit expression of the molecule but will prevent it from anchoring to the surface.

BRIEF DESCRIPTION OF THE DRAWINGS

Figure 1:
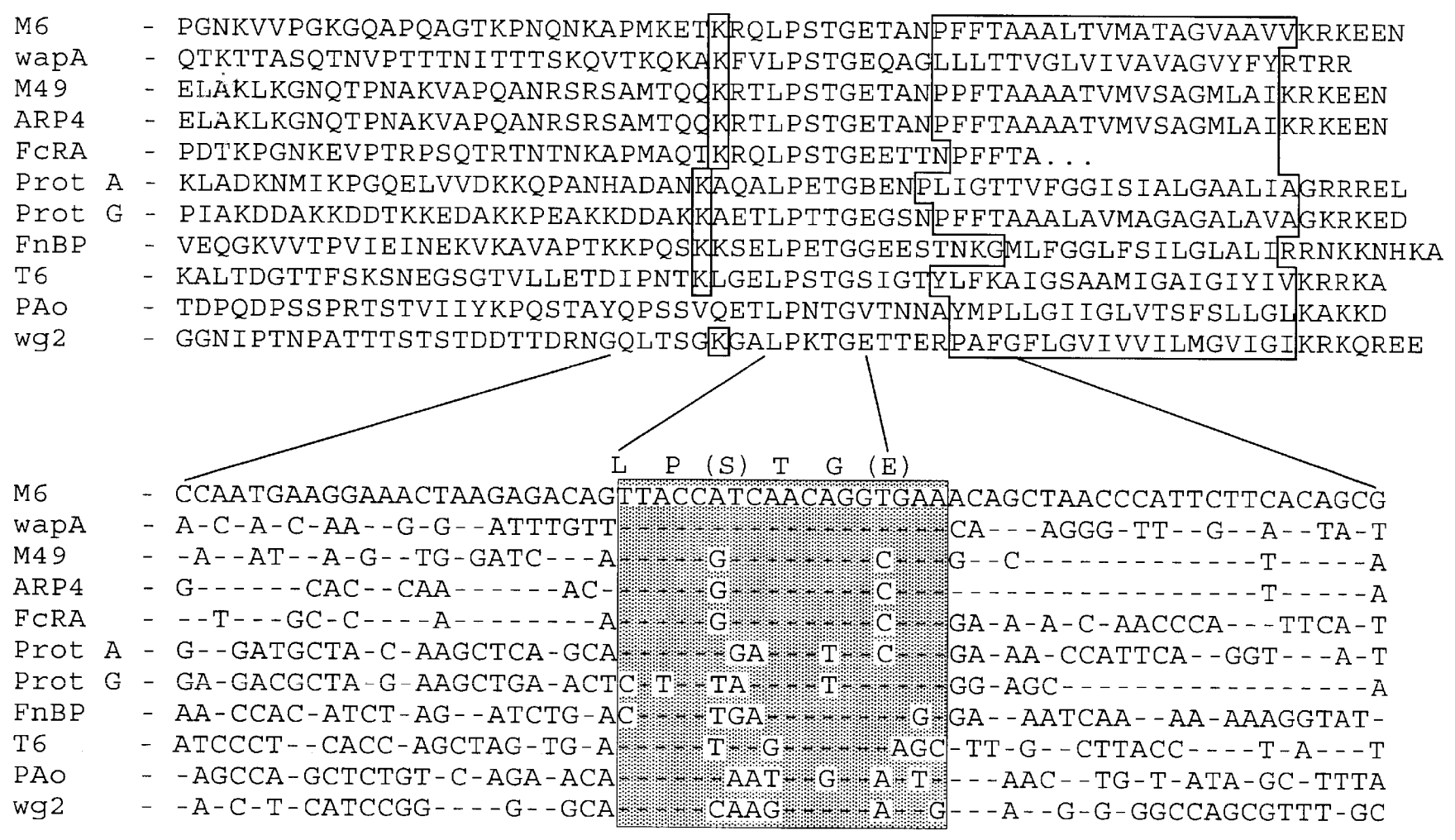

FIG. 1 shows the alignment of the amino acids in the C-terminal regions of a variety of surface antigens from gram-positive bacteria and the gene segments which are employed to express them. The LPSTGE motif (SEQ ID NO:36) is shaded and the proteins were aligned along this consensus sequence. In 10 out of 11 proteins, a conserved lysine residue was found 2 or 3 residues preceding the consensus LPSTGE sequence (SEQ ID NO:36) (boxed). The homologous carboxyterminal hydrophobic regions are also boxed. Abbreviations used in the left column are the same as those in Table 1.

Careful study of FIGS. 2 and 3 will assist in understanding this invention. FIG. 2 represents a model of the M protein with certain of the positions and segments identified. FIG. 3 identifies each amino acid residue in the complete structure of the M6 protein.

Figure 2:
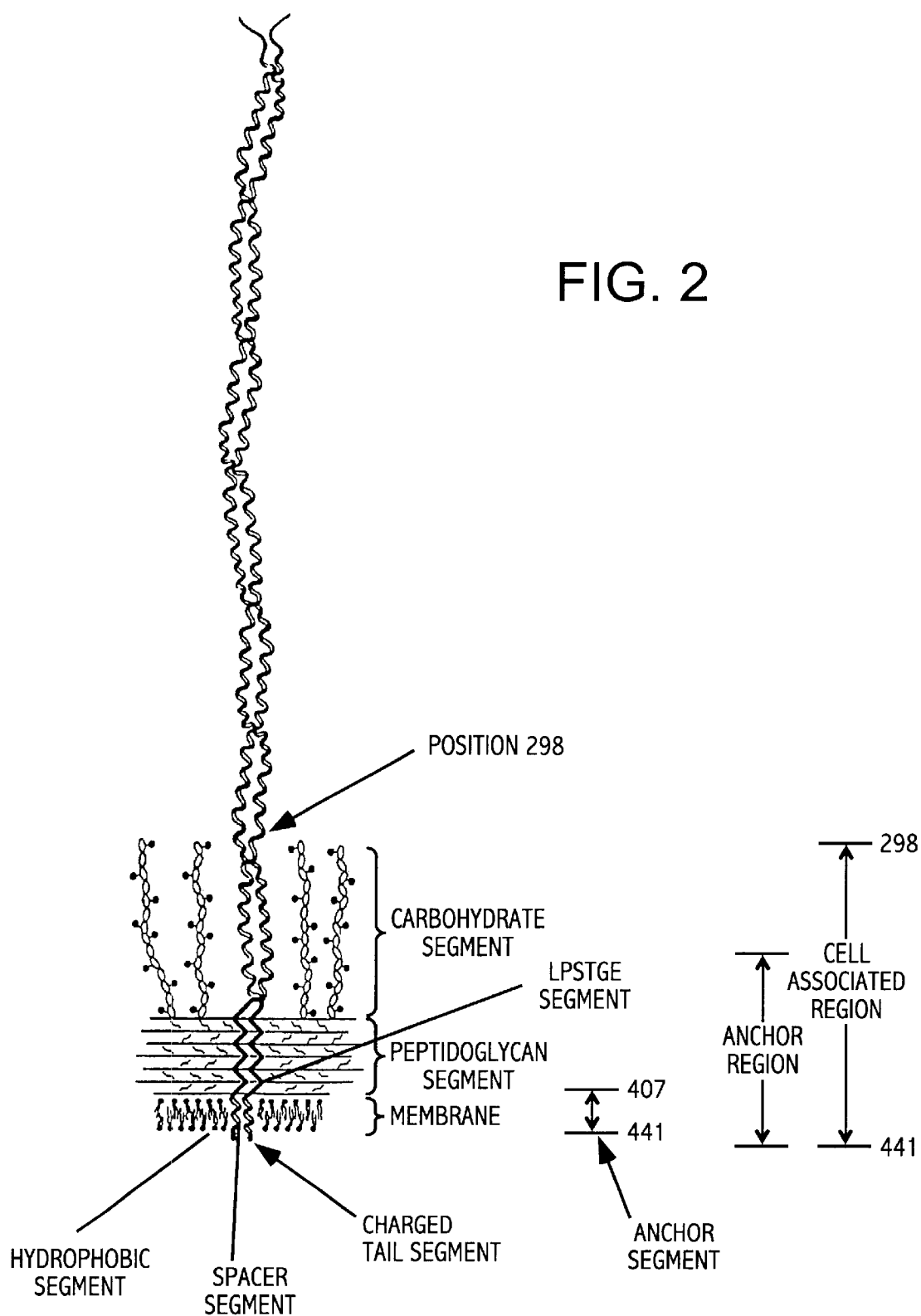
FIG. 2 a model of the M protein.

It will be understood from the foregoing discussion that the segment of the M protein identified as the cell associated region in FIG. 2 is analogous to regions for surface proteins found on other gram-positive bacteria such as those listed in Table 1. As discussed above, there is a high degree of homology particularly within the anchor sequence especially the LPXTGX segment (SEQ ID NO:37) found in all gram-positive surface proteins. As will be described below, and for the purpose of illustrating this invention, the gene segment spanning region 122 to 300 of the gene which expresses the M protein is genetically removed and replaced by a new gene segment expressing a foreign protein, for example, an antigen which will generate useful antibodies, thereby producing a novel hybrid surface protein. Because of the great degree of homology within the cell associated regions of all gram-positive bacteria, the hybrid gene can be employed in any gram-positive bacteria. The selected bacteria will express the desired hybrid protein using the anchor region to attach the molecule to the cell and positioning the inserted active segment on the cell surface. The inserted active segment is hereinafter referred to as the "active polypeptide".

The term "active polypeptide" is used herein in the broadest possible sense. It refers to any peptide, polypeptide or protein which may be delivered to an animal host for any useful purpose. For example, as described in detail hereinafter, the cell associated region of a protein from gram-positive bacteria can be fused to a segment of a viral protein from a pathogen to produce a hybrid surface protein which will be expressed by non-pathogenic bacteria. The bacteria can colonize an animal host and function as a vaccine. It will elicit antibodies in an animal host to protect against or inhibit subsequent infection by the virus. The fused viral segment is the "active polypeptide" of that particular embodiment of the invention.

For convenience, the term "polypeptide" will hereinafter be used to refer to molecules which are of sufficiently high molecular weight to be called proteins, to products of lesser molecular weight, usually called polypeptides, and to products of even lesser molecular weights normally referred to as peptides.

The "active polypeptide" may be any polypeptide which can be delivered to an animal host for a useful purpose. It could be, for example the viral segment referred to above. It could also be an antigen, from any pathogenic virus, or from a bacteria, parasite or fungi. In such instances, the active polypeptide may be the complete antigen, the antigenic determinant of the antigen or a segment of the antigen which includes the antigenic determinant. The useful purpose will be to elicit a protective immune response by the production of antibodies or to elicit a cellular immune response to the antigen.

Figure 3B:
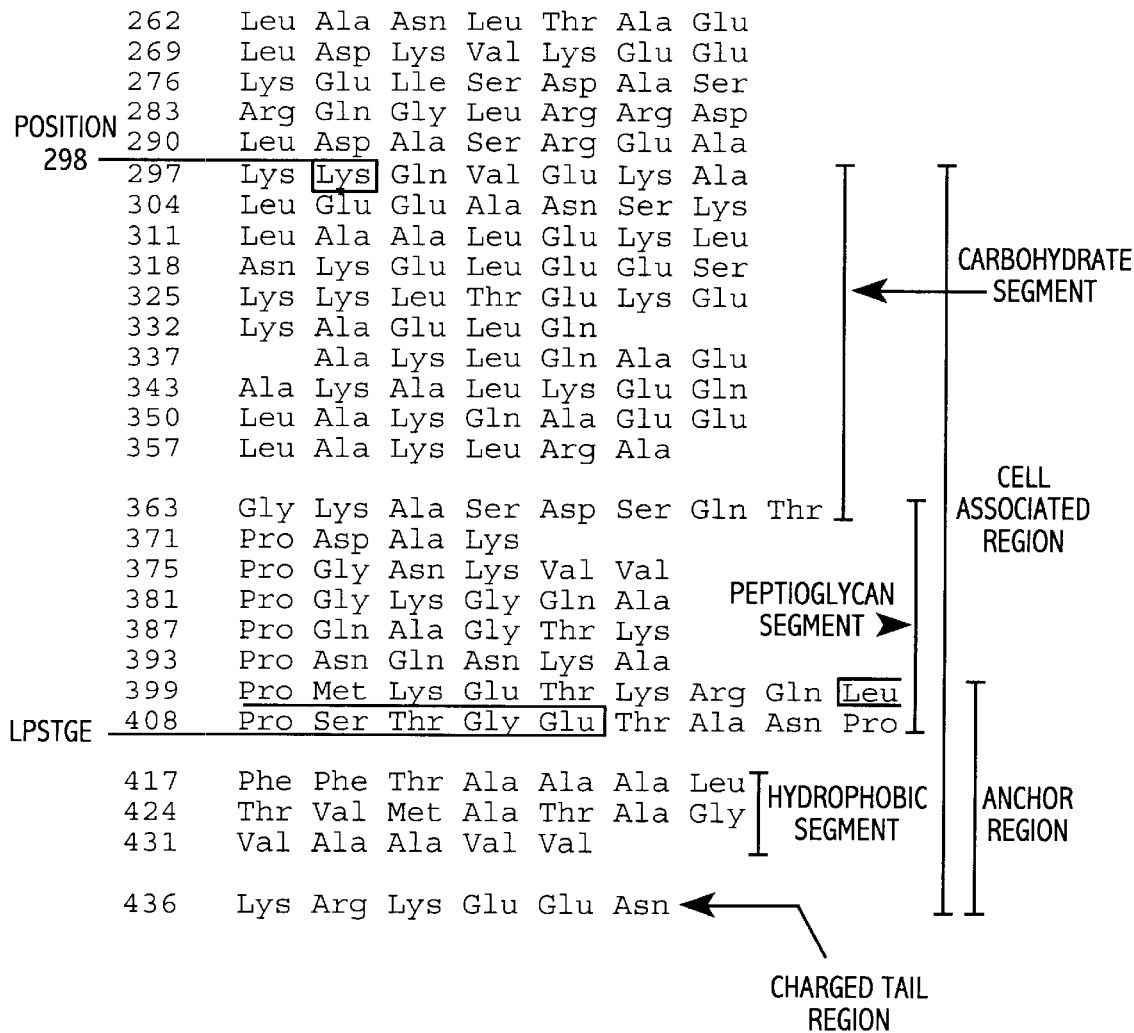
FIG. 3 shows the complete amino acid sequence of the M6 protein.
Figure 10:
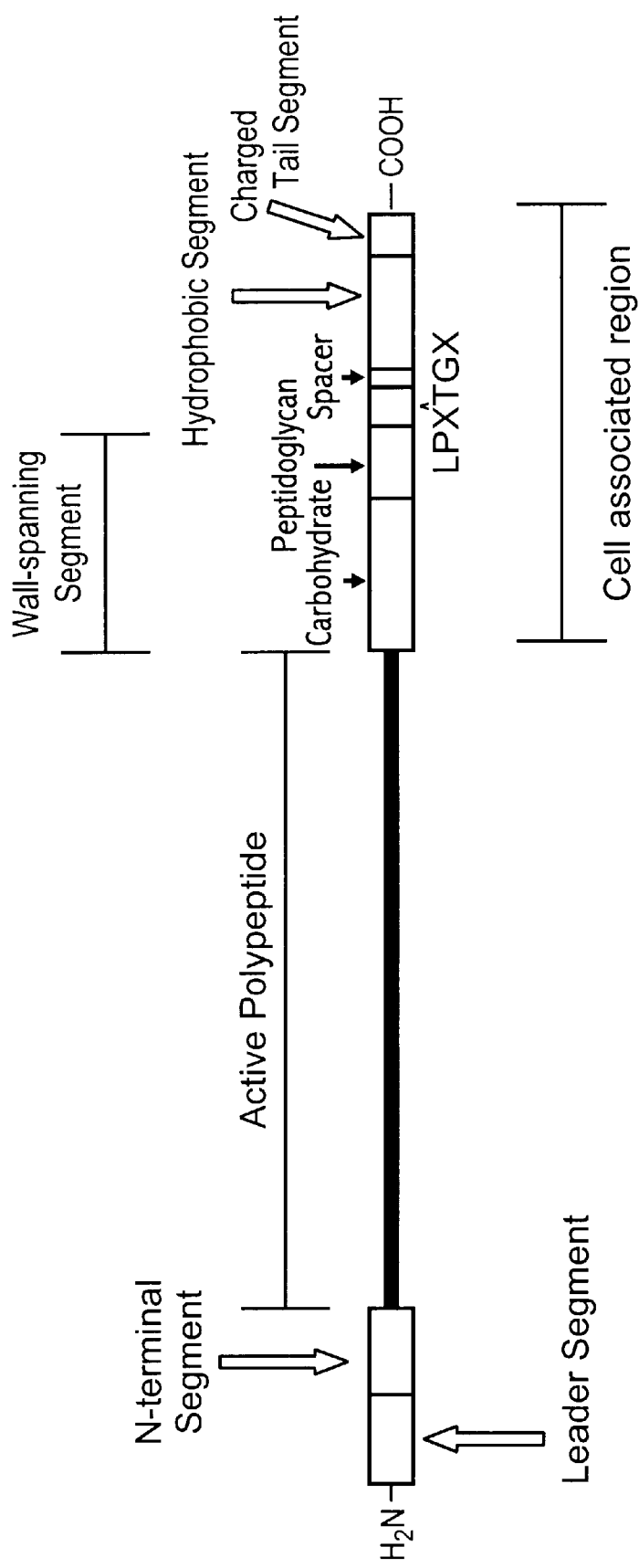
FIG. 10 shows a typical hybrid protein of the invention.
Figure 11A:
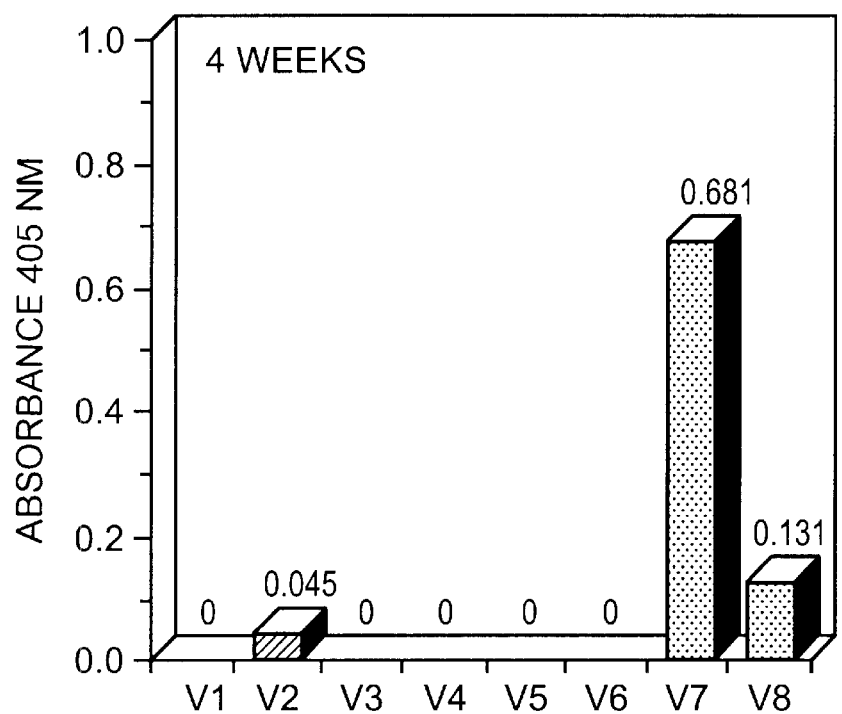
FIGS. 11 and 12 show the results of studies in which mice were treated with a hybrid protein of the invention.
Figure 11B:
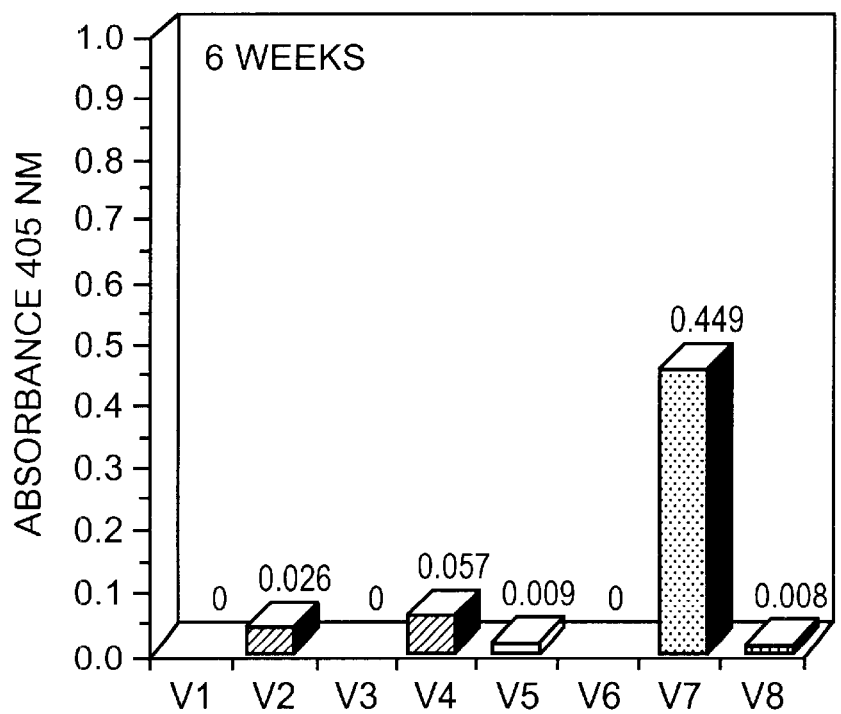
Figure 11C:
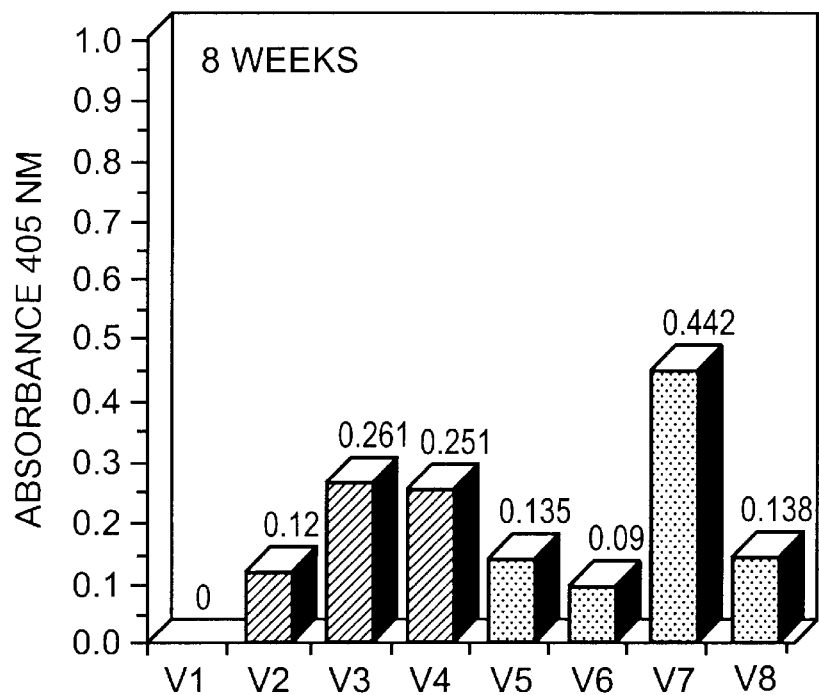
Figure 11D:
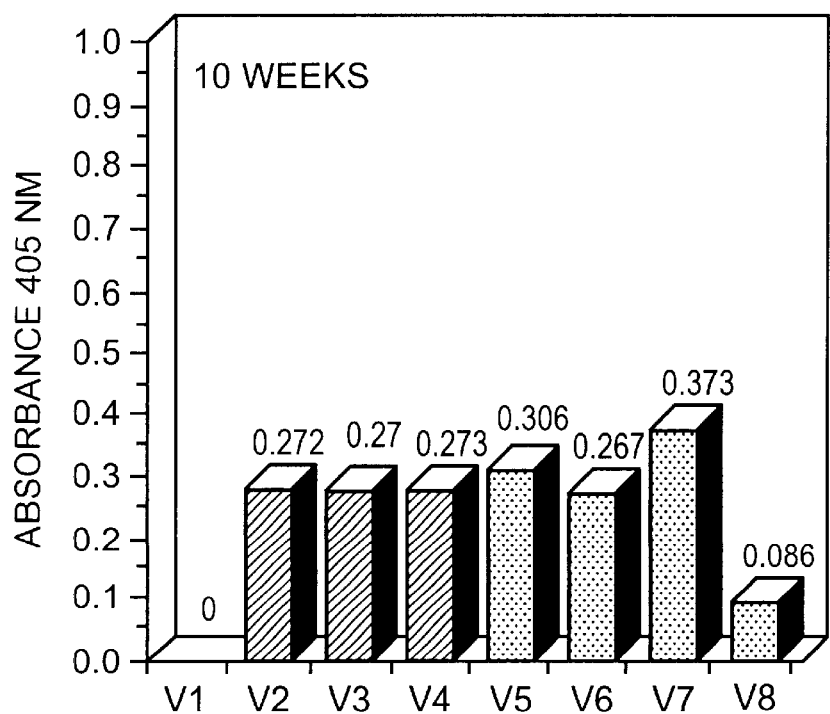
Figure 12A:
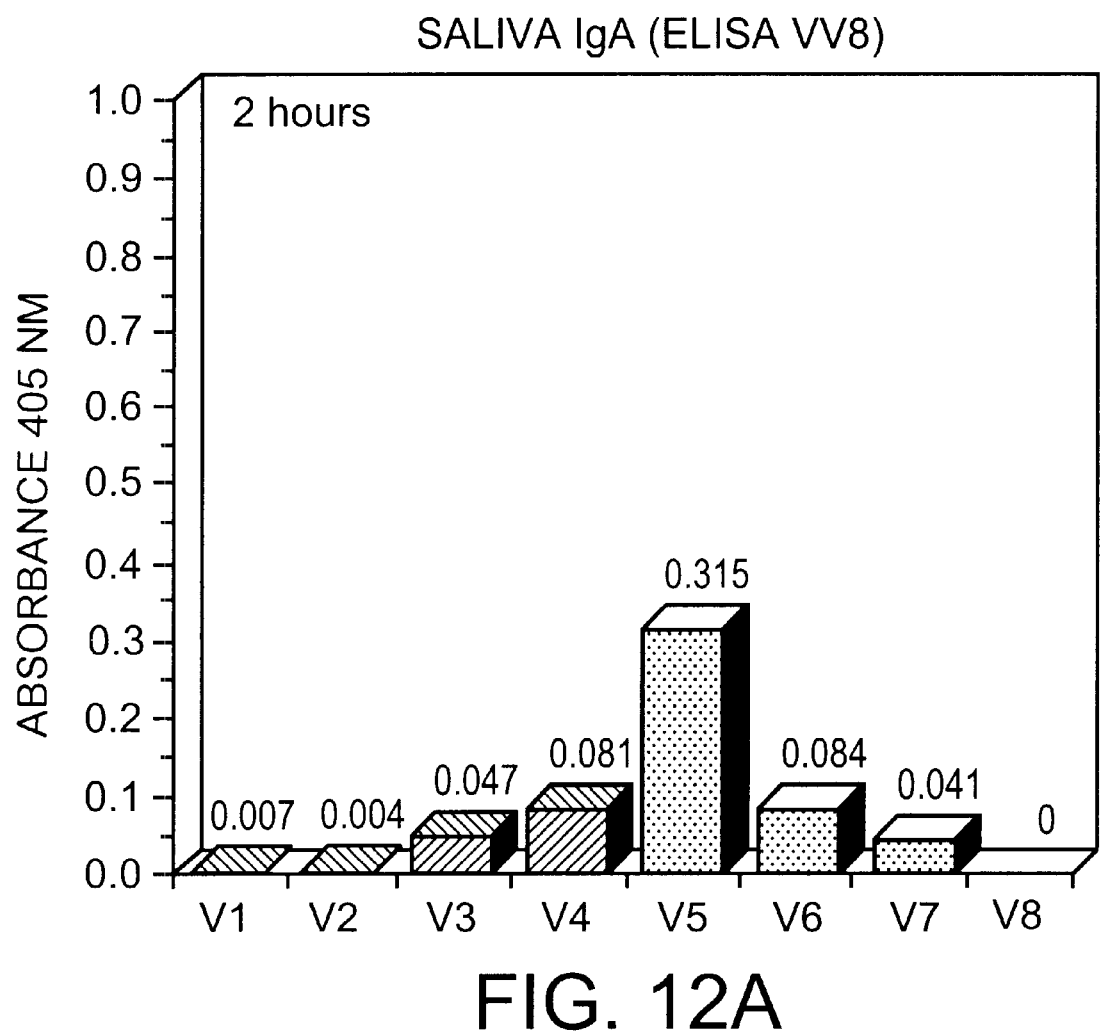
Figure 12B:
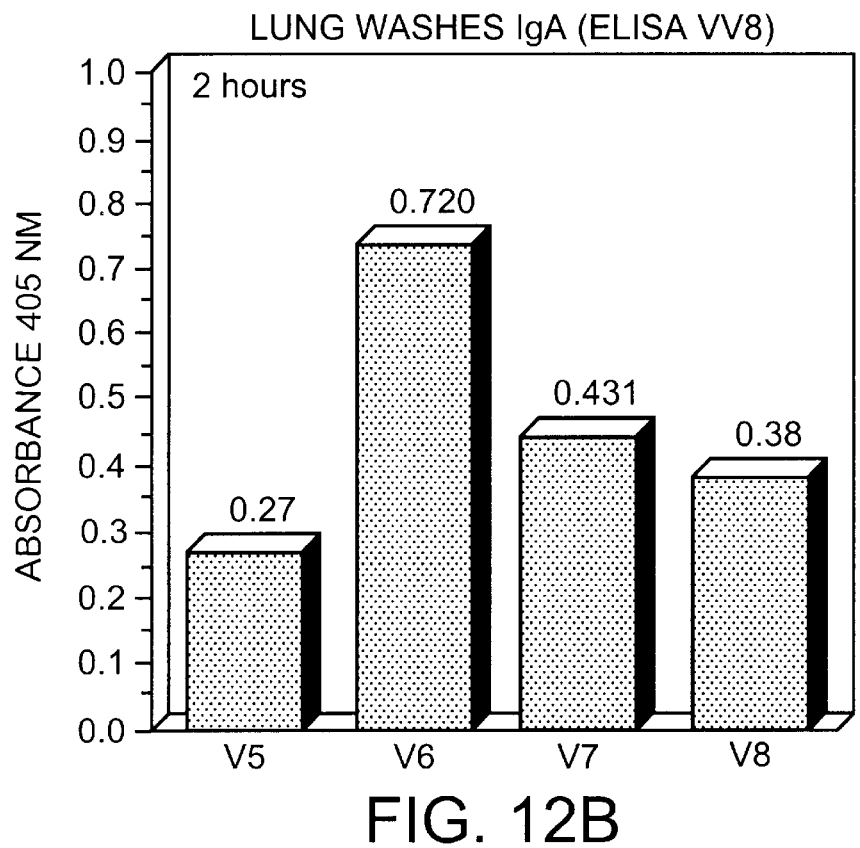
Figure 12C:
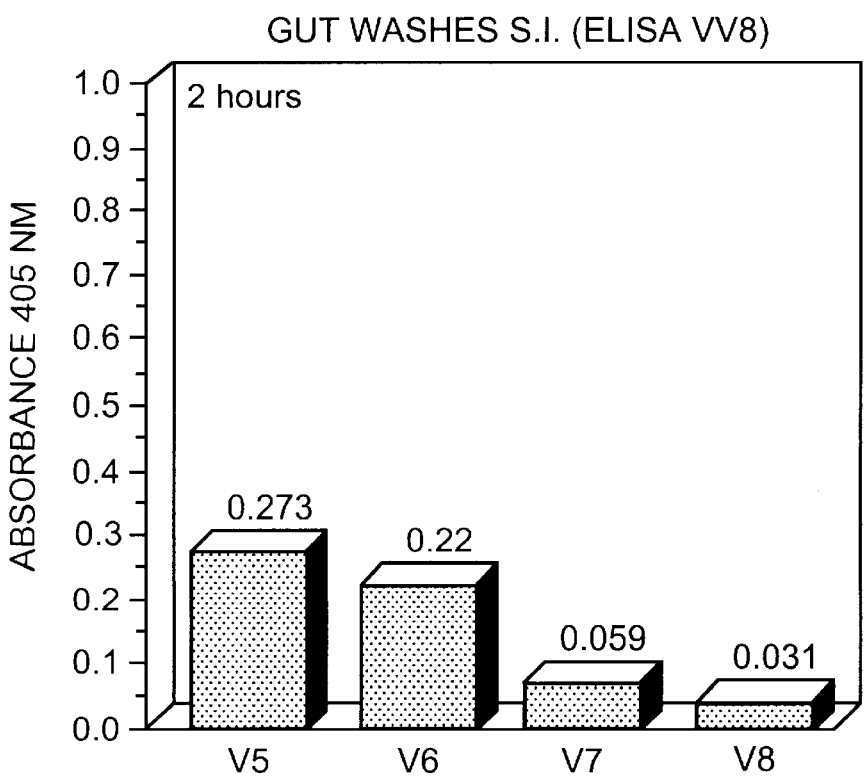

The term "cell associated region" as used in this specification and claims will be readily understood by reference to the figures, especially FIGS. 2, 3 and 10. It will be seen that the cell associated region includes a cell wall spanning sequence of amino acid residues and a carbohydrate spanning segment. The wall spanning sequence may be omitted from the hybrid proteins of this invention, although it is presently preferred not to do so.

The cell associated region also includes the anchor region which contains the anchor segment (LPXTGX (SEQ ID NO:37)), the spacer segment, the hydrophobic segment and the charged tail segment. The anchor sequence is essential to the hybrid proteins of this invention. Without this sequence, the hybrid protein will not be retained on the surface of the gram positive bacterial carrier.

FIG. 10 shows the balance of a typical hybrid protein of the invention which, as shown, includes the active polypeptide fused to the cell associated region. The figure also shows a leader segment and a small N-terminal segment at the amino terminal of the active polypeptide. These segments cooperate in the proper placement of the hybrid protein on the surface of the gram positive bacteria. The function of the leader segment is to permit the proper processing of the hybrid protein within the cell. The N-terminal segment in cooperation with the leader segment enables the leader peptidase enzyme to separate the leader segment from the N-terminal segment and permit the hybrid protein to assume its proper position on the surface of the bacteria. The leader segment and the N-terminal segment are from the same surface protein as the protein of the cell associated region. The N-terminal segment suitably contains the first few amino acid residues derived from the amino end of the protein used in the cell associated region of the hybrid protein. About ten such residues are normally sufficient for the proper processing, but segments containing up to twenty or more amino acid residues may be employed.

The active polypeptide is not necessarily an antigen from a pathogenic organism. It may also be an enzyme, for example. In that event, the useful purpose will be to deliver the enzyme on the surface of a non-pathogenic bacteria to a specific site in the animal host colonized by that non-pathogenic bacteria.

The active polypeptide may be the complete molecule which comprises the enzyme. Alternatively, it may be only that segment of the polypeptide which is required to accomplish the useful purpose.

The active polypeptide may be an antigen which will react with antibodies elicited by pathogenic microorganisms. Bacteria of the invention carrying such active polypeptide antigens are useful as diagnostic reagents.

When reference is made herein to non-pathogenic bacteria it should be understood to include gram positive commensal bacteria as well as pathogenic bacteria which have been modified or attenuated by the usual procedures so that their pathogenicity is weakened or destroyed and which express hybrid proteins in accordance with the process described herein, such hybrid proteins containing a C-terminal region including the LPXTGX region (SEQ ID NO:37).

BRIEF DESCRIPTION OF THE INVENTION

This invention provides non-pathogenic gram positive bacteria which express at least one hybrid surface protein the C-terminal region of which is attached to the bacteria. The C-terminal region includes, but is not limited to, the cell associated region of a surface protein normally expressed by a gram-positive bacteria which may be pathogenic or non-pathogenic. The balance of the hybrid surface protein includes an active polypeptide which may be delivered to an animal host for any useful purpose. The surface protein "normally produced" by the bacteria of this invention refers to the whole protein produced by the bacteria before it is genetically altered in accordance with the process of this invention.

As is known from previous studies (29) and indicated in FIGS. 2 and 3, amino acids 298–441 of the M protein are buried within the cell whereas residues 1–297 are exposed on the surface of the bacterial cell. In accordance with this invention, by employing genetic manipulations described and illustrated herein, nearly all of the surface exposed region of the M protein may be removed and replaced by an active polypeptide that is linked to the C-terminal cell-associated region of the M protein to produce a hybrid surface protein of the invention. Because the cell associated region is essentially the same for all gram-positive surface molecules (FIG. 10), a smimilar strategy may be used whereby the cell associated region of any one of these molecules may be used as a delivery carrier or vehicle to deliver an active polypeptide from another source. The new gene employed to express the hybrid surface protein may be inserted into a plasmid by standard techniques and the plasmid used to transform an *Escherichia coli* or other vector. The *E. coli* thereafter will express the new fusion protein, i.e. the hybrid protein of this invention. The *E. coli* procedure is useful for the production of large amounts of hybrid protein which can be isolated from the periplasm of this gram negative organism. However, for most utilities of this invention, it is preferred to transform a gram positive organism for the production of the hybrid protein on the surface of the gram positive bacteria. The recombinant genes produced in accordance with the invention may be processed by any gram positive bacteria.

Alternatively, the newly constructed plasmid containing the fusion gene may be used to integrate the fusion gene into the chromosome of a gram-positive bacteria, for example the chromosome of *Streptococcus mutans*. The newly produced strain of *Streptococcus mutans* will thereafter produce the new hybrid protein of this invention by expressing it on the cell surface. This is the presently preferred procedure for producing the products of this invention.

Antigenic polypeptides from a wide variety of microorganisms may be employed as the active polypeptides of the invention. These include pathogenic microorganisms which infect man and animals. There follows a representative list of typical microorganisms which express polypeptides useful in the practice of this inventions. The transformed bacteria of the invention may be used to treat or prevent the diseases associated with infection by the microorganism.

Fungi: *Candida albicans, Aspergillus fumigatus, Histoplasma capsulatum* (all cause disseminating disease), *microsporum canis* (animal ringworm) Parasitic Protozoa: *Plasmodium falciparum* (malaria), *Trypanosoma cruzi* (Sleeping sickness), Spirochetes: *Borrelia bergdorferi* (Lyme disease), *Treponema pallidum* (syphilis), *Borrelia recurrentis* (recurring fever), *Leptospira icterohaemorrhagiae* (leptospirosis)

Bacteria: *Neisseria gonorrhoeae* (gonorrhoea), *Staphylococcus aureus* (endocarditis), *Streptococcus pyogenes* (rheumatic fever), *Salmonella typhosa* (salmonellosis), *Hemophilus influenzae* (influenza), *Bordetella pertussis* (whooping cough), *Actinomyces israelii* (actimomyosis), *Streptococcus mutans* (dental caries)

*Streptococcus equi*—Strangles (Horses), *Streptococcus agalactiae* (bovine mastitis), *Streptococcus anginosus* (canine genital infections)

Viruses: Human immunodeficiency virus (HIV), Polio virus, Influenza virus, Rabies virus, Herpes virus, Foot and Mouth Disease virus, Psittacosis virus, Paramyxovirus, Myxovirus, Coronovirus In one embodiment of this invention, a non-pathogenic gram-positive bacteria that is a commensal organism for the host animal will be used to express the hybrid protein on its surface, by inserting the gene coding for the hybrid protein into the non-pathogenic gram-positive bacteria. If the fusion is with an active polypeptide that is an antigen from a pathogenic organism (bacterial, viral, parasitic, or fungal), and the resulting commensal bacteria expressing the hybrid antigen is administered to an animal host, there will be an immunological response by both humoral and cell mediated pathways. One possible immunological response is the production of antibodies, thereby effecting protection against infection by the pathogen. If the fusion is with an enzyme, the enzyme will be expressed on the surface of the commensal. A wide variety of active polypeptides may be delivered to the surface of gram positive. bacteria as will be apparent to the skilled artisan from a study of this disclosure.

The genes, plasmids, chromosomes, and transformed bacteria of this invention are produced by the application of standard recombinant techniques well known to those skilled in the art. For example, an oligonucleotide or a restriction fragment coding for a viral coat protein, the virulence factor of a bacterial surface antigen (or, in fact, the complete antigen), an enzyme or other desired progenitor of a hybrid surface protein of the invention may be ligated to the gene which expresses the cell associated region of the M protein or other known surface protein from a gram positive bacteria such as those listed in Table 1. The resulting hybrid gene will be used to transform a gram positive bacteria to effect the production of a surface hybrid protein of the invention.

This invention will be further explained in conection with the expression of the hybrid protein M6:E7 by the GP246 strain of *Streptococcus gordonii*. This hybrid antigen contains the C-terminal cell associated segment of the M6 protein. The antibody eliciting polypeptide, E7, is an early protein from a papillomavirus strain.

*Streptococcus gordonii* is a commensal bacteria of the oral cavity. E7 is a 98 amino acid early protein produced during viral replication of human papillomavirus type 16 (HPV16). It is an oncoprotein, antibodies to which are found in patients with cervical cancer. It is considered a major candidate antigen for vaccines against HPV-induced malignant neoplasias.

The novel bacteria of this invention may be produced by standard homologous recombination shown in FIGS. 4 and 5. As illustrated, a new strain of *Streptococcus gordonii*, GP232 which expresses large quantitites of M6 protein was employed as the host to produce a new strain GP246.

The procedure employed as illustrated in FIGS. 4 and 5 is standard and widely utilized by the skilled practitioner. The technology, as illustrated, is to construct a gram positive recipient organism for the insertion of the fusion gene in a random location in the chromosome that results in a high expression of the fusion gene. The insertion site may vary from organism to organism and even within the same organism. The advantage of the method is that it insures that the inserted gene is in a site which will result in high expression of the fusion gene, rather than rely on the expression as a result of a foreign promoter. Thus, the method assures that a region with a strong promoter is selected.

In the process of producing the novel GP246 strain, the 538 base pair segment between sites KpnI and HindIII of the M6 protein was excised from the novel plasmid pVMB20, produced as described below, and the 294 base pair encoding for E7 was inserted in its place to produce the novel gene which was utilized for the production of the new plasmid pVMB21. The region of the M protein that was excised results in the placement of the E7 molecule at the cell surface with a 120 amino acid segment of the M6 N-terminus including the leader segment fused to the N-terminus of E7. The construct was made in *E. coli* and the recombinant plasmid was used to transform *S. gordonii* by the standard double cross-over procedure with GP232 to effect chromosomal integration of the gene which expresses the M6:E7 protein by the new strain GP246.

MATERIALS AND METHODS

Recombinant DNA techniques. Gene fusions in *Escherichia coli* vectors were obtained and constructed by standard procedures (30).

Streptococcal transformation. Frozen cells of naturally competent *S. gordonii* Challis were prepared and transformed by known procedures (31). Plating and scoring of transformants on multilayered plates was performed using erythromycin at a concentration 5 ug/ml in the overlay using known procedures (32).

Genetic analysis of transformants. Transformants were streaked on the surface of 3 blood agar plates by toothpick transfer of colonies from the selection plate. The first plate contained erythromycin (5 ug/ml), the second chloramphenicol (5 ug/ml), and the third had no antibiotic. Plates were incubated 36 hours at 37° C. After incubation, a nitrocellulose membrane was applied to the surface of the plate that contained no antibiotic, and kept for 20 min. at room temperature. The membrane was then incubated 30 min at 37° C. and 15 min at 80° C. in a vacuum oven. The presence of E7 protein bound to the nitrocellulose was detected using anti-E7 polyclonal antibodies (1:5000 dilution), obtained from rabbits immunized with a MS2:E7 fusion protein produced in *E. coli* (33).

Immunofluoreseence. Bacteria grown in Todd-Hewitt broth (Difco) were harvested in late exponential phase, applied on a glass slide, and fixed with methanol. Slides were treated with M6- or E7-specific antibodies (1:50 dilution), extensively washed, and then reacted with goat anti-rabbit (or anti-mouse) IgG antiserum (1:100 dilution), conjugated with rhodamine. Results were observed under a Con-focal Fluorescence Imaging System MRC-500 Bio-Rad microscope.

Western blot analysis of cell extracts. Streptococci were grown to late stationary phase in Todd-Hewitt borth (Difco).

Cells were harvested and resuspended in 50 mM Tris(pH 8.0), 50 mM $MgCl_2$, 30% sucrose. Protoplasts were obtained by treating the cell suspension with lysozyme (100 ug/ml) for 30 min. at 0° C. Protoplasts were then centrifuged and resuspended in 50 mM Tris (pH 8.0). Thorough lysis was achieved by five cycles of quick freezing/thawing of the suspension. Cells that did not lyse and gross debris were discarded by low speed centrifugation at 1,000 rpm for 15 min, whereas the supernatant, containing membranes and cytoplasm, was used for Western blot analysis. The extract obtained from about $5 \times 10^8$ streptococcal cells was run on a gel, and Western blot was performed by conveniotnal methods.

Immunization of nice. Balb/c mice were immunized subcutaneously with $5 \times 10^8$ live GP246 streptococcal cells ($5 \times 10^7$ colony forming units) emulsified in complete Freund's adjuvant. Two and three weeks after the primary immunization, animals were given subcutaneous boosters of the same bacterial dose emulsified in incomplete Freund's adjuvant. Animals were bled a week after the last boost.

RESULTS

Production of the plasmid pVMB3: A construct was made where ermC, a gene conferring resistance to erythromycin (34), was cloned adjacent to emm-6.1, so that both genes would be within the same ClaI fragment. In this construct the initiation codon of emm-6.1was 19 bp downstream of one of the ClaI sites, so that ClaI cleavage would leave emm-6.1 promoterless. Plasmid pVV3:M6 (35), containing this ClaI site upstream of the emm-6.1coding sequence, was used in the experiments. The 2.0 kb MspI fragment of pE194, containing ermC, was ligated with a partial ClaI digestion of pVV3:M6. After transformation of *E. coli* DH5, a clone was isolated with a plasmid, pVMB3, contaiing the ClaI fragment.

Production of the strain GP230: The 3.4-kb ClaI fragment of pVMB3, containing ermC and the promoterless emm6.1, was ligated with chromosomal DNA of *S. gordonii* also cut with ClaI. The ligation mixture was used to transform the naturally transformable *S. gordonii* "Challis", strain V288. By this method the emm-6.1/ermC ClaI fragment was integrated at random into the chromosome. The chromosomal DNA ligated to the ClaI fragment provided the homology for integration during transformation. Erythromycin-resistant (Em-r) transformants were selected and analyzed for production of M6 protein by "streak blots". Of 700 Em-r transformants, 196 (28%) produced M6 protein. Based on the semiquantitative dot blot analysis, GP230 appeared to be the best M6 producer.

Production of the strain GP232: *S. gordonii* GP230 was transformed with the chromosomal DNA of pneumonococcal strain GP69. This pneumonoccal strain is resistant to chloramphenicol but susceptible to erythromycin produced according to the procedure of Pozzi and Guild (36). When GP69 chromosomal DNA is used to transform GP230, recombination occurs at the level of the ermC sequence leading to insertion of the CAT sequence into the copy of ermC integrated into the GP230 chromosome. This insertion yields GP232 which, as discussed and shown in the figures, expresses M6 on its surface and is also resistant to chloramphenicol and sensitive to erythromycin. *S. gordonii* strain GP232 has been deposited with the American Type Culture Collection, 10801 University Blvd., Manassas, Va. 20110–2209, pursuant to the terms of the Budapest Treaty, and assigned Accession No. PTA434.

Figure 4:
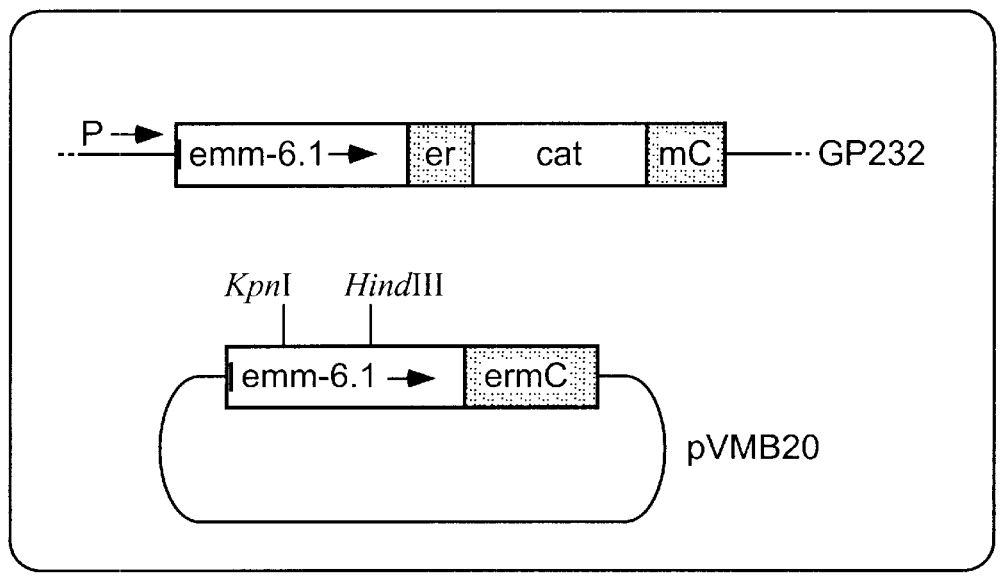
FIG. 4 shows the host vector system GP232-pVMB20.

Expression of E7 protein of KPV16 in *S. gordonii*: The integration vector, pVMB20, was constructed to allow insertion of heterologous DNA sequences into the emm-6.1 gene present on the chromosome of GP232. pVMB20 is a novel *Escherichia coli* plasmid that does not replicate in Streptococcus and carries emm-6.1 and the erythromycin resistance marker ermC. The vector pVMB20 has been deposited with the American Type Culture Collection, 10801 University Blvd., Manassas, Va. 20110–2209, pursuant to the terms of the Budapest Treaty, and assigned Accession No. PTA433. The host-vector system GP232-pVMB20 is shown in detail in FIGS. 4 and 5. Specifically, the novel plasmid pVMB20 and novel bacteria *S. gordonii* GP246 were prepared by the following procedure.

Figure 5:
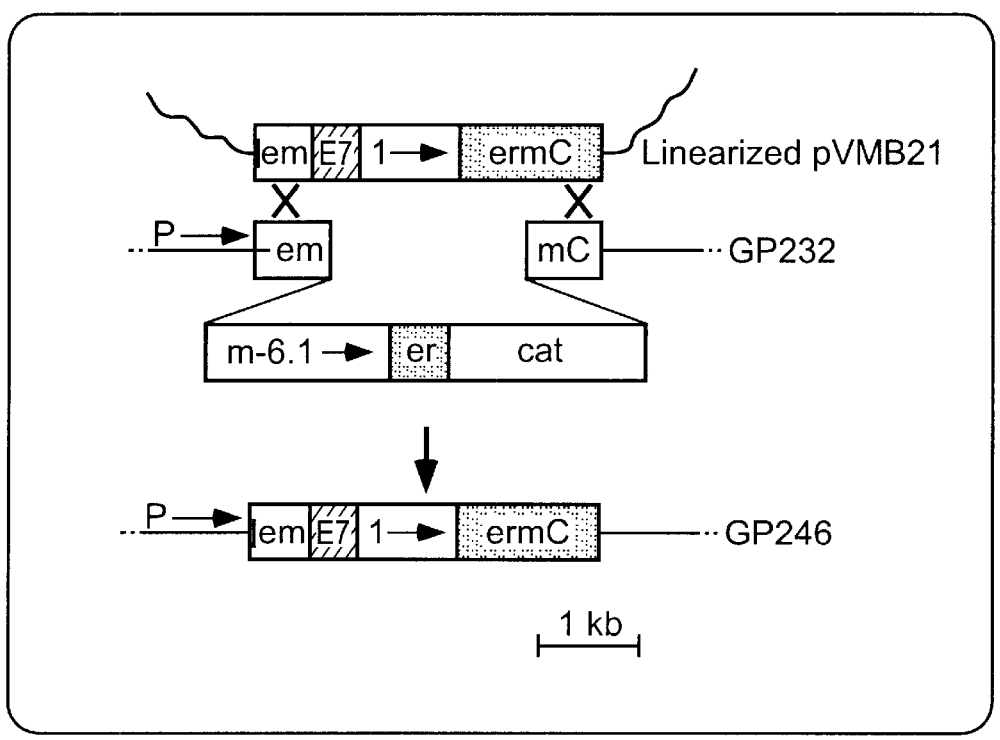
FIG. 5 shows the construction and chromosomal integration of the M6:E7 translation fusion in GP246.
Figure 6A:
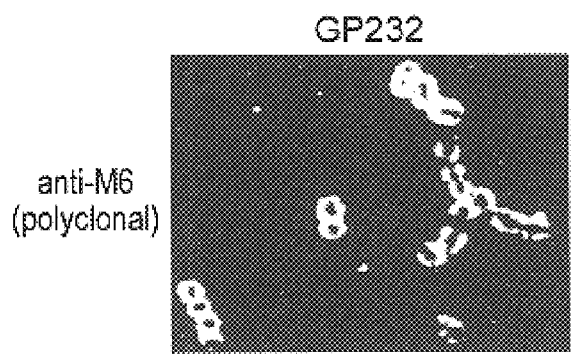
FIG. 6 shows the results of studies designed to demonstrate that the M6:E7 fusion protein expressed in Streptococcus gordonii GP246 located on its surface.
Figure 6B:
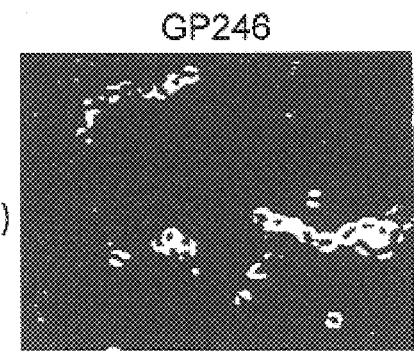
Figure 6C:
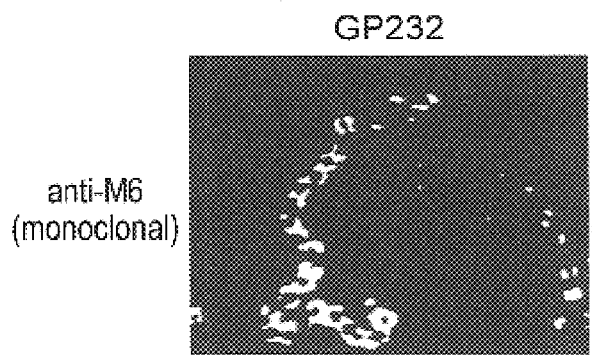
Figure 6D:
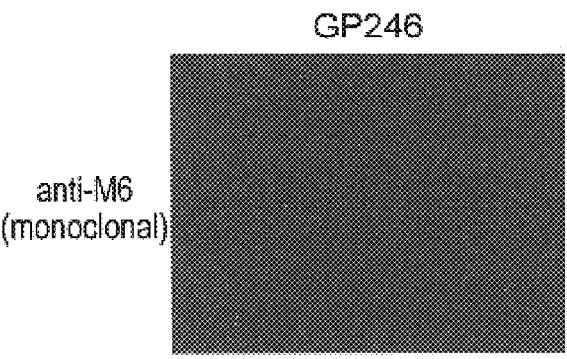
Figure 6E:
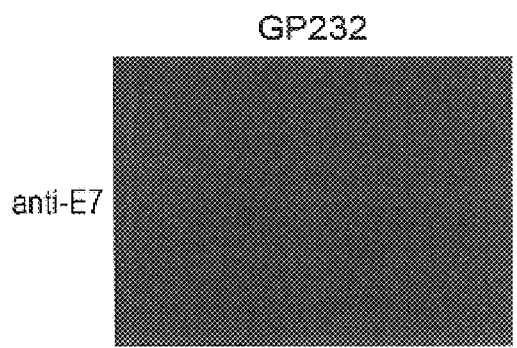
Figure 6F:
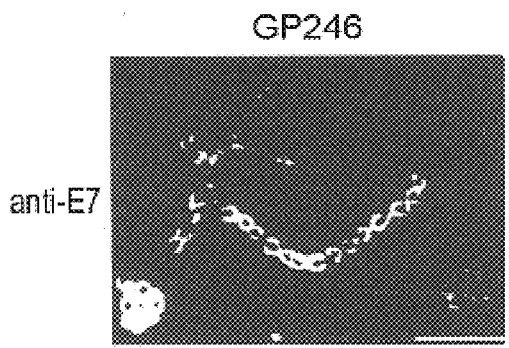

Host-vector system for heterologous gene expression: [A] In the chromosome of the novel host strain *S. gordonii* GP232, a copy of the M6 protein gene (emm-6.1)(37), promoterless but with its own ribosomal binding site was integrated downstream of a strong chromosomal promoter. Adjacent to emm-6.1 is found ermC (34), whose coding sequence is interrupted by insertion in its BclI site of the 1.8-kb MboI fragment of pC221 containing a cat gene (38). GP232 expresses M6 on its surface and is resistant to chloramphenicol and sensitive to erythromycin. It was obtained using transformation to integrate heterologous DNA into the streptococcal chromosome. The structure is shown in the figure. The size (5.2-kb) of the heterologous DNA integrated into the chromosome in GP232 was determined by Southern blot analysis. The integration vector pVMB20, is a 6.3-kb *E. coli* plasmid that does not replicate in Streptococcus. It was obtained by subcloning in pBLUESCRIPT (Stratagene, La Jolla, Calif.) a 3.4-kb ClaI fragment of plasmid pVMB3 containing emm-6.1 and ermC by the procedure explained below. This is the same ClaI fragment which is integrated into the chromosome of GP232, the only difference being that in GP232 ermC is interrupted by cat. When pVMB20 is used as donor DNA in transformation of competent cells of *S. gordonii* GP232, erythromycin-resistant transformants are obtained by recombination between the integration vector and the homologous chromosomal sequences. The DNA fragment containing the cat gene is deleted in the chromosome of these transformants, whereas an intact ermC gene is restored. (FIG. 5)

(B) The E7 protein gene of HPV16(39) was cloned into the emm-6.1 sequence of pVMB20 to yield pVMB21. pVMB20 was digested with KpnI and HindIII and ligated with a KpnI/HindIII segment containing the E7 sequences obtained by in vitro DNA amplification (polymerase chain reaction) performed on plasmid pMBS21L/E7 (33). Amplification primers were designed in order to obtain "in frame" insertion of the 294 bp encoding for E7 into emm-6.1. Nucleotide sequence analysis of pVMB21 confirmed the expected structure of the M6:E7 translational fusion. pVMB21 was linearized and used to transform GP232. E7 was found to be expressed in 6% of the erythromycin-resistant transformants. In these transformants integration of the pVMB21 sequences produced a deletion involving the cat gene. The structure of GP246, a representative transformant, was confirmed by Southern blot analysis. The nucleotide sequence of the junction fragments of the M6:E7 gene fusion present on the chromosome of GP246 was also determined after cloning in pBLUESCRIPT the ClaI fragment containing the M6:E7 fusion.

Surface expression of the E7 protein: Expression of the E7 protein of HPV16 in *S. gordonii* on the surface of strain GP246 was verified by immunofluorescence using antibodies specific for either the M6 protein carrier or the E7 insert. GP246, containing the M6:E7 gene fusion exhibited positive fluorescence when reacted with either M6-specific or E7-specific polyclonal antibodies (FIG. 6), confirming the surface location of the E7 molecule and the M protein on the surface of *S. gordonii*. No fluorescence was observed when GP246 was reacted with known monoclonal antibody 10All, which is specific for an epitope of M6 whose coding region was contained in the KpnI/HindIII fragment deleted in the construction of M6:E7 gene fusion (FIG. 6).

Figure 7:
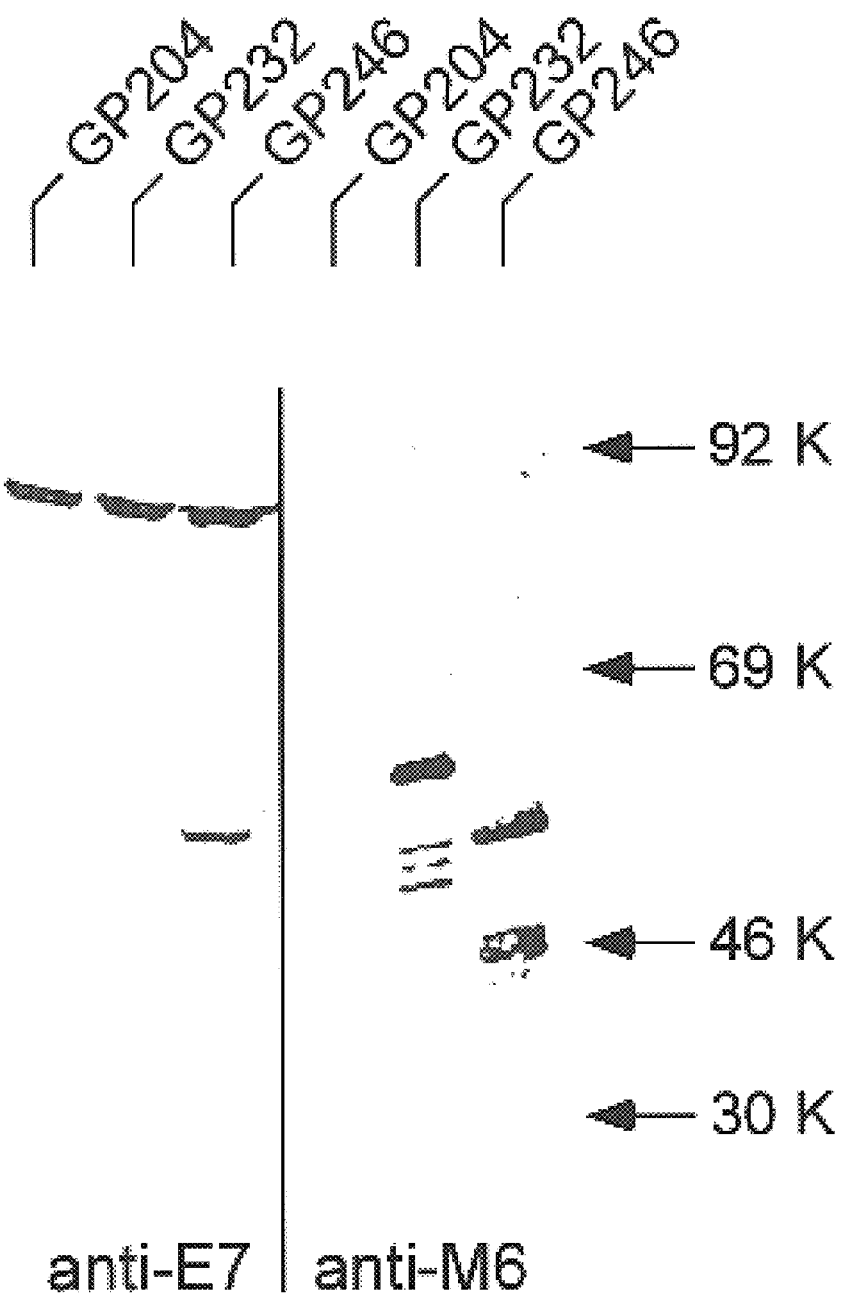
FIG. 7 shows that cell extracts of recombinant Streptococcus gordonii246 expresses the M6:E7 fusion protein.

To demonstrate that the E7-expressing recombinant streptococci in fact produce an M6:E7 fusion protein, *S. gordonii* cell extracts were analyzed by Western blot (FIG. 7). In cell extracts of GP246, the same bands reacted with E7- and M6-specific antibodies, whereas no E7-specific reactivity was found in the recipient GP232, whose extracts showed M6-specific reactivity (FIG. 7).

Substantially the same procedures used to construct M6:E7 a hybrid protein containing the C-terminal region of the M6 molecule and allergen-5 was successfully expressed on the *S. gordonii*. Western blots of the cell wall extract using allergen-5 specific antibodies established (as with M6:E7) that allergen-5 was indeed expressed in the cell wall fraction of the *gordonii*. Allergen 5 was obtained as described by Fang, et al. (66).

Figure 8:
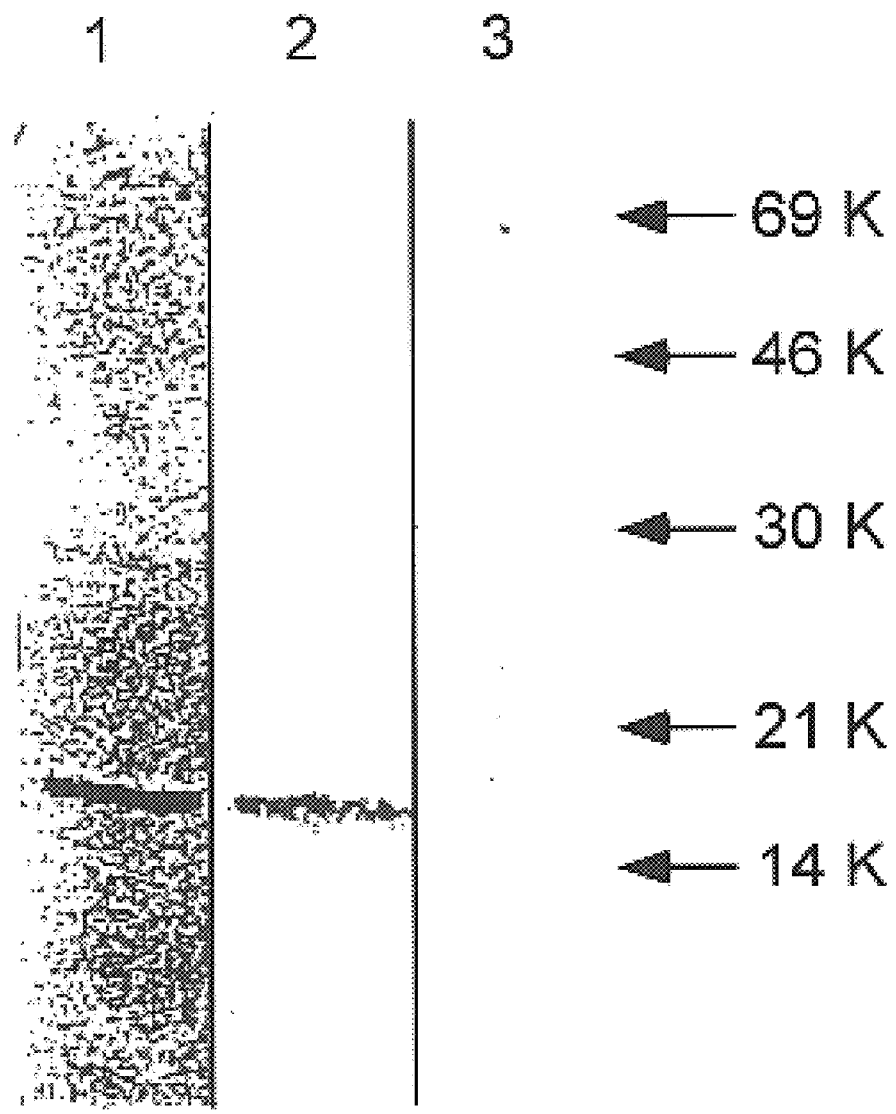
FIG. 8 shows that animals immunized with the recombinant GP246 produce antibodies reactive with the E7 protein.
Figure 9:
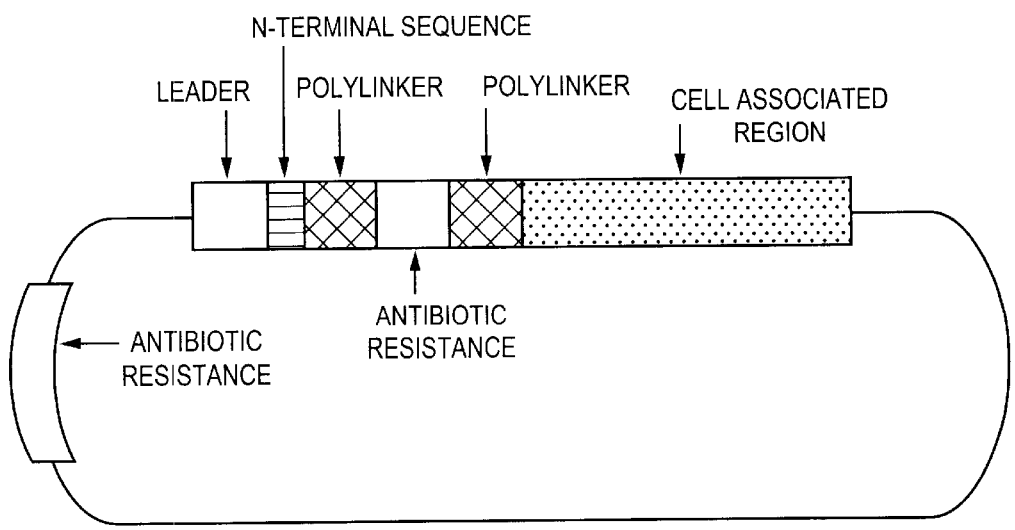
FIG. 9 shows a universal plasmid of the invention.

Immune response to fusion protein on streptococcal surface: The immunogenicity of the M6:E7 fusion protein was examined by immunizing mice with recombinant *S. gordonii* GP246 expressing the M6:E7 fusion protein. Control mice were immunized with the isogenic strain GP232 which express M6 protein. Sera from three animals immunized with each strain were pooled and tested by Western blot for their reactivity with purified E7 protein produced in *Schizosaccharomyces pombe*. FIG. 8 shows that animals immunized with strain GP246 containing surface M6:E7 produced antibodies reactive with the E7 protein, indicating that E7 protein is immunogenic when expressed as a fusion protein on the streptococcal surface. No antibodies to the E7 protein were seen in the sera of mice immunized with GP232 containing only M6.

The procedure which has been described permits the production of the non-pathogenic bacteria *S. gordonii* GP246 or other transformed gram positive bacteria which express a hybrid surface protein such as the novel hybrid surface antigen M6:E7. This novel antigen is a hybrid protein, the carboxy terminus of which is attached to the bacteria and is substantially the same C-terminal region normally found in other gram-positive surface proteins as explained above. The active polypeptide of this hybrid surface protein is the antigen E7 of HPV 16. When the bacteria is administered, e.g. by colonization, to an animal host in need of protection, the active polypeptide will elicit both humoral and cell mediated responses resulting in the production of a protective immune response against infection by papillomavirus.

It will be noted that the heterologous antigen of the hybrid surface protein of this invention prepared as described above is a viral antigen produced during viral replication. Thus, the process of this invention makes possible the production of novel gram positive bacteria for the delivery of viral antigens to an animal in sufficient quantities to elicit a protective immunogenic response to infection by a virus.

The novel M6:E7 and novel intermediate products of this invention are produced from two starting materials. These are pVV3:M6 and GP69. They can be prepared by the procedures described in the cited references. Therefore the novel products can all be obtained from known materials utilizing the procedures described herein. However, to assist in the practice of the invention and without admitting any necessity to do so pVV3:M6 and GP69 have been deposited at the American Type Culture Collection under the accession numbers ATCC 68003 and ATCC 68929, respectively.

The foregoing M6:E7 example illustrates the utilization of a non-pathogenic commensal gram positive bacteria normally present in the mammalian oral cavity to protect the whole body against viral infection. Analogously prepared non-pathogenic bacteria can be used to express and deliver other useful antigens by the processes described are illustrated herein. For example, protein antigens on the surface of mammalian tumors can be fused with the cell wall associated region of a surface antigen of any gram positive bacteria, the fusion gene inserted in a gram positive commensal, and the resulting bacteria employed as a vaccine to generate tumor specific immune responses useful in tumor therapy.

These examples illustrates only one aspect of the invention. The invention, in fact, provides a delivery system for any kind of polypeptide which may be useful to raise an immune response in an animal or for other useful purposes.

When utilized as a vaccine, the selected transformed commensal will be employed to colonize a mammal. It will produce the selected hybrid surface protein, the active polypeptide segment of which will elicit the production of protective antibodies.

Gram positive non-pathogenic bacteria normally found on the vaginal mucosa may be employed as contraceptives. For this utility, surface antigens of male sperm can be employed as the active polypeptide on the hybrid surface protein of the bacteria *Lactobacillus acidophilus* normally found on the surface of the vaginal or uterine mucosa. When the transformed bacteria are utilized to colonize such mucosa, the hybrid proteins will elicit the production of antibodies to the surface antigens of the sperm and bring about inactivation of the sperm. In effect, the sperm will be viewed by the female body as a foreign substance and the preformed antibodies will react with and inactivate the sperm cells.

There are two important advantages to this type of contraception. One is that, since the sperm will be inactivated, the ova will not be fertilized. The other is that the contraceptive effect can be neutralized simply by treating the immunized female with an antibiotic to clear the gram positive bacteria expressing the hybrid antigen.

Still another utility of the transformed bacteria of this invention is the delivery of a surface antigen from an HIV virus to the surface of a gram-positive commensal organism to provide a vaccine which may be used to prevent AIDS. For this utility, the polypeptide GP120, the V3 loop of GP120, GP160 or a related surface antigen or segments of such antigens such as sequence 735 to 752 of GP16 or RP135 a 24-amino acid segment of GP 120 from the HIV virus. These polypeptides will be fused to the leader and at least a portion of the N-terminal sequence of a gram positive surface protein and its anchor region for delivery to the surface of the commensal bacteria. When the transformed commensal expressing the HIV antigens on its surface is delivered to a susceptible mammal, an immune response is raised to protect against infection by HIV virus. Furthermore, by using a recombinant vaginal commensal to deliver an HIV antigen such as GP120 to the vagina, the IgA antibodies produced to this antigen are protective against infection at this site. IgA antibodies in vaginal secretions will reduce the number of HIV particles in the secretions of an HIV positive female and thus reduce the spread of AIDS.

The products of this invention are useful in densitization therapy. This type of therapy is widely employed to alleviate the discomfort of atopic individuals who develop exaggerated IgE responses to antigens (called allergens in the allergy field). The increased production of IgE antibodies is believed to be a principal cause of the allergic responses such as hay fever, asthma, and anaphylactic shock.

The allergens may arise from any of a variety of sources including foods, molds, dust and animal furs. Flora such as roses or rag weed are a major source of allergens. The "sting" of vespids such as wasps, yellow jackets and hornets contain allergenic proteins.

The conventional therapy employed to ameliorate the immune response from exposure to allergens has been hyposensitization treatment which involves repeated injections of increased doses of allergen. This causes an increase in allergen specific IgG antibodies which blocks the binding of allergen specific IgE to mast cells.

A number of allergens-specific peptides and proteins have been identified, isolated, and cloned. Those include, for example, allergin 5, a vespid venom protein. These allergens can be included as the active polypeptide of the hybrid surface proteins of this invention. Commensal bacteria which generate such hybrid proteins may be used to colonize an allergic patient. The result will be a constant source of allergens which will elicit the same protective immuned response as achieved with desensitization therapy.

The formation and expression of the hybrid protein M6:allergen 5 has been described above. FIGS. 11 and 12 show the results of immunization studies utilizing this hybrid surface antigen.

FIG. 11 illustrates the serum IgG response of mouse sera to purified allergen-5 in the hybrid surface protein. Mice were immunized either intradermally with *S. gordonii* expressing hybrid surface allergen-5 ($10^7$ CFU) in Freund's adjuvant or intranasally with the same organisms. Animals were bled at 4, 6, 8, and 10 weeks after immunization and the serum checked by ELISA for IgG to purified allergen-5. Both mice immunized intradermally (V1–V4, hatched bars) and animals immunized intranasally (V5–V8, closed bars) expressed antibodies to the allergen. Control animals immunized with gordonii without surface exposed allergen-5 showed no response to the allergen. All animals immunized intranasally with the recombinant *gordonii* remained colonized for at least 12 weeks as determined by swabs and still expressed the allergen 5 for this period. All assays were performed with a 1:50 dilution of sera.

FIG. 12 shows the IgA response to allergin-5 in intranasal and intradermally immunized animals. Twelve weeks after immunization (intradermally or intranasally) with *gordonii* expressing allergin-5 (see FIG. 11) saliva was taken and the animals sacrificed to obtain lung and gut washes. The saliva and washes were analyzed for the presence of IgA specific for allergen-5 by ELISA. Results revealed that salivary IgA was present in the intradermal and intranasal immunized animals with a better response in the intranasally colonized animals. The best IgA response was seen in the lung washes of the intranasally colonized animals. While an IgA response was seen in the small intestine of the gut (S.I.), they were lower than the lung washes. All assays were performed with a 1:1 dilution of the samples.

A particular advantage of the systems for delivery of the hybrid surface proteins of this inventions is that since the transformed organisms are normal commensals, they will continue to colonize and act as a constant stimulus of a protective immune response thereby avoiding the need of continual immunization.

The skilled artisan can readily conceive of numerous other applications of the novel products of this invention. For example, non-pathogenic gram positive bacteria can be produced to deliver surface antigens which will elicit protective antibodies against a wide variety of disease states including malaria, measles, pertussis and retroviral infections such as AIDS, coccidiosis, distemper, fowl pox and bruccelosis.

Another particular advantage of the delivery system of this invention when used as vaccine is that live bacteria are employed. As is known, live bacteria stimulate a much stronger immune response than attenuated or dead bacteria. Still another advantage is that, because non-pathogenic bacteria are employed, the vaccine is safe. Still another is that several methods of administration are possible.

The invention is not limited to *S. gordonii* as the carrier bacteria or even to streptococcus, in fact other non-pathogenic gram-positive bacteria may often be preferred. For example, bacteria normally present on the intestinal mucosa (*Enterococcus fecalis*) may be preferred to deliver an active polypeptide to the intestine.

Moreover, the invention is not limited to the surface expression of one hybrid surface protein containing only one epitope. The carrier organism may be transformed by well known procedures to express a plurality of hybrid surface proteins each with a different active polypeptide or, alternatively, to express a hybrid surface protein in which the active polypeptide includes more than one epitope.

Thus far this invention has been described and illustrated principally with respect to the delivery of antigens to elicit protective antibodies but, as indicated above, the invention is not so limited. For example the invention can be used to deliver enzymes.

Humans deficient in the enzyme lactase which is secreted in the small intestine are unable to properly hydrolyze lactose into its components, D-glucose and D-galactose. One result is that they are unable to digest milk or milk products properly. Heretofore, the treatment has been life long ingestion of tablets or other therapeutic dosage forms containing the missing enzyme. In accordance with the practice of this invention, commensal intestinal bacteria are provided which are cloned to produce a hybrid protein, the active polypeptide of which is lactase. The bacteria may be employed to colonize the intestinal mucosa for the continual production of the required enzyme.

*Streptococcus mutans* are major organisms responsible for tooth decay. They secrete glucosyltransferases which hydrolyze sucrose to produce glucose. The glucose, in turn, is formed into glucan polymers which adhere to the tooth surfaces and participate in the decay process. Utilizing the procedures described and claimed herein, *S. mutans* can be transformed to express hybrid surface proteins containing glucanase enzymes. The transformed bacteria may be employed to colonize the oral cavity and inhibit the formation of glucan polymers thereby protecting against tooth decay. Alternatively, *Streptococcus mutans* may be transformed to produce enzymes that digest dental plaque, thus preventing the initiation of decay.

The process of this invention substantially as describes above was employed utilizing *Staphyloccus aureus* as the bacteria for expression of the surface protein. When the anchor region (containing the LPXTGX segment, hydrophobic segment and charged tail segment) of Protein A, a surface molecule of this bacteria was fused to the enzyme alkaline phosphatase (a dimeric periplasmic protein of *E. Coli*) and the gene for this fusion placed back in *S. aureus*, the molecule was found to be translocated to the outside of the cell and anchored to its surface. The details of this procedured are found in Reference 65 which is incorporated herein by reference.

The skilled artisan will recognize that several variations of this invention are possible without departing from its spirit or scope.

One variation which is particularly useful, especially for the production of vaccines is to include an adjuvant in the hybrid protein and the necessary nucleotide sequence for the expression of the desired protein in the gene used to generate the protein. Typically, a plasmid could be produced in which the gene for expressing the cholera toxin B subunit which is a known mucosal adjuvant is inserted between the C-region polypeptide and the active polypeptide. Alternatively, the gene for the subunit could be inserted upstream of the active polypeptide. This orientation may elicit an enhanced IgA response because in the usual interaction of CTB and the cell which produces antibodies, the CTB directly contacts the cell and stimulates the production of antibodies for the antigen for which CTB is functioning as an adjuvant. The plasmid may be employed in the double cross-over technique illustrated in FIGS. 4 and 5 to incorporate the hybrid gene into the chromosome of a gram positive bacteria for the expression of a hybrid protein of the invention on the bacterial surface. Other immune enhancing proteins may be used instead of the cholera toxin B subunit to enhance the immune response to an active polypeptide.

The transformed bacteria of this invention are useful in diagnostic tests. They may be used, for example, to test for the presence of antibodies characteristic of a specific infection in the plasma of infected animals.

Conventionally, the procedure of testing for an infection caused by, for example, *Neisseria gonorrhoeae* requires the isolation and purification of an antigen which will react with a specific antibody characteristic of the infecting microorgansim and suspected to be present in the plasma. The antigen is then incubated with plasma or other body fluid. If a reaction takes place, it can be recognized by any of a variety of known tests.

In the standard enzyme linked immunoassay procedure, the isolated and purified antigen is adhered to a solid phase glass or plastic substrate. It is then exposed to the body fluid such as plasma or serum. If the fluid contains an antibody characteristic of the infecting organism, an antigen/antibody reaction will take place. The reaction product will remain on the solid phase which is then incubated with an anti-antibody tagged with a detectable enzyme such as horseradish peroxidase.

The transformed bacteria of this invention can be employed as the source of the antigen used in the diagnostic test. In such tests, the transformed bacteria is employed as an antigen. The skilled artisan will be familiar with several diagnostic tests of this nature. Such use, in accordance with this invention, eliminates the necessity of isolating and purifying the antigen as required by prior art methods.

For diagnostic testing, a transformed bacteria of the invention is prepared in which the active polypeptide includes an epitope for a specific antibody which is characteristic of the microorganism causing the infection. The bacteria is adhered to the solid phase and the balance of the diagnostic test is conducted in the usual manner. Of course the test is not limited to the use of enzymes to detect the presence of antibody utilizing, for example, the ELISA assay. Other labels such a radioactive isotopes can be employed.

Diagnostic kits can be provided containing the transformed bacteria, typically in a lyophilized form to be reconstituted, together with the other reagents normally provided with such kits. These may include an aqueous buffer, a labeled anti-antibody, sterilized water and, possibly, other reagents. Alternatively, the transformed bacteria, either in aqueous suspension of lyophilized may be provided for use in the diagnostic test together with other reagents to be provided by the laboratory conducting the diagnostic test.

The various segments of the hybrid surface proteins of the invention are not necessarily adjacent to each other in the protein or in the gene used to produce it. It may be convenient for any of a number of reasons apparent to the skilled artisan to separate the nucleotides on the hybrid gene used to express the protein by insertion of other nucleotides thereby to express hybrid proteins in which the active polypeptide and the cell associated polypeptide are separated by a selected spacer. It is not essential that the complete segment from the cell associated region of the surface antigen be employed in constructing the hybrid surface protein of the invention so long as an anchor region beginning with the LPXTGX segment and ending at the charged tail segment is present to anchor the hybrid polypeptide to the bacteria that expresses it.

FIG. 9 shows one especially useful embodiment of this invention. It illustrates a universal plasmid containing a polylinker site. A polylinker is an oligonucleotide or DNA sequence which contains several. restriction sites and therefore can be employed for the insertion of genes excised by a variety of restriction enzymes. For example, the plasmid can be constructed with a polylinker insert containing several restriction sites such as EcoRI, ClaI, HindIII, XboI, PstI, BamHI or any of several others. Such polylinkers are either commercially available or may be readily constructed by the artisan.

To produce a plasmid of this invention the polylinker insert will be ligated into a plasmid already containing the selected gene segment for expressing the desired cell associated segment of the hybrid protein to be produced. The plasmid is shown as containing the leader sequence for the hybrid antigen, but such sequence is not necessarily in the plasmid. It may be included in the oligonucleotide sequence used to express the active polypeptide. Although the various gene segments in the plasmid are shown as adjacent to each other, they may be separated by spacers.

The plasmid is shown as containing two different antibiotic resistant regions to assist in selection. One, which is located within the polylinker site, separates it into two sections and will be removed when replaced by an insert. Other markers such as those resulting in color may be employed. Other formulations of a plasmid with polylinker sites may be constructed as required.

The plasmid without the marker which separates the linker, but with an effective promoter, can be employed to transform a gram positive bacteria. The plasmid shown can cross over with a chromosome as described above. A transformed bacteria containing the plasmid or the chromosome will express the desired surface hybrid protein.

The plasmid M6.1 367-441 which is described and claimed in the above identified parent application is especially useful in the practice of this invention. The preparation of this plasmid is described in the parent application. It has been deposited in *E. coli* strain K561 at the American Type Culture Collection under the accession number ATCC68235.

As explained in the parent applications, this plasmid can be fused with an appropriate DNA sequence and the hybrid gene inserted in an appropriate carrier, such as *E. coli* or a selected non-pathogenic gram positive bacteria. The resulting transformed bacteria will express a polypeptide of this invention. The transformed gram positive bacteria may be used directly as a vaccine. Alternatively, it can be used in a cross-over reaction as explained above to produce another transformed bacteria which will express the desired polypeptide more efficiently. The plasmid may also be used for the production of a unviersal peptide by the insertion of a polylinker.

A special advantage of the invention is that the recombinant gram positive bacteria may be delivered to the animal in need at the mucosal site at which the pathogen normally invades the body. These includes oral as well as nasal, intestinal and vaginal sites. Such delivery will stimulate a local immune response at the site and be an effective means to raise a protective immune response to the pathogen. Since the bacteria employed will be non-pathogenic, normal organisms for that particular site, they may be employed without danger of toxic effects. The selected bacteria can be administered to fish or wild animals by mixing it in the food they eat or the water they inhabit.

Utilizing the same procedures described above, hybrid proteins can be prepared containing the antibody eliciting antigens shown in the following Table 2 as active polypeptides. The table shows the polypeptide, which will produce antibodies protective against infection by a pathogen, the disease to be protected against and the publication which describes the polypeptide. In some instances the gene used to elicit the oligonucleotide coding for a peptide will need to be prepared and inserted in a plasmid. The procedures are completely parallel to the procedures described above. The C-terminal anchor region can be any of those specifically suggested above, or any other anchoring segment of a surface protein from a gram-positive bacteria described in Table 1. The active polypeptide of the transformed bacteria will include the peptide shown, fused to the leader sequence and a small segment of the N-terminus of a surface protein to permit proper translocation to the cell surface.

TABLE 2

[SEQ ID NOS.: 3–12 AND 56–58]
PEPTIDE SEQUENCES SUITABLE FOR DEVELOPMENT
OF VACCINES FROM HYBRID ANTIGENS

| Peptide | | Pathogen/Disease (protein) | Ref | SEQ ID NO: |
|---|---|---|---|---|
| A. | H-(ASN-Ala-ASN-Pro)n-OH n 3 | Malaria, cs protein of *Plasmodium falciparum* | 39 | 56 |
| B. | H-(Gly-Asp-Arg-Ala-Asp-Gly-Gln-Pro-Ala)n-OH n 2 | Malaria, cs protein of *Plasmodium vivax* | 40 | 57 |
| C. | Glu-Gln-Asn-Val-Glu-His-Asp-Ala | Malaria, Pf 155 of *Plasmodium falciparum* | 41 | 58 |
| D. | Asn-Ala-Glu-Asn-Lys-Glu-Glu-Leu-Thr-Ser-Ser-Asp-Pro-Glu-Gly-Gln-Ile-Met | Malaria, Merozoite surface protein of *Plasmodium falciparum* | 42 | 3 |
| E. | Met-Gln-Trp-Asn-Ser-Thr-Ala-Phe-His-Gln-Thr-Leu-Gln-Asp-Pro-Arg-Val-Arg-Gly-Leu-Tyr-Leu-Tyr-Leu-Pro-Ala-Gly-Gly | Hepatitis, pre S(1) | 43 | 4 |
| F. | Asp-Pro-Arg-Val-Arg-Gly-Leu-Tyr-Phe-Pro-Ala-Gly-Gly-Ser-Ser-Ser-Gly-Thr-Val | Hepatitis, pre S(2) | 44 | 5 |
| G. | Cys-Thr-Lys-Pro-Thr-Asp-Gly-Asn-Cys-Thr-Cys | Hepatitis Surface antigen | 45, 46 | 6 |
| H. | Tyr-Ser-Thr-Leu-Tyr-Arg-Trp-Leu-Asp-Asp-Ser-Phe | Poliovirus, replicase protein | 47 | 2 |
| I. | Asn-Ala-Pro-Ser-Lys-Thr-Lys-Leu-Glu-Pro-Ser-Ala-Phe | Poliovirus, replicase protein | 48 | 8 |
| J. | Lys-Lys-Pro-Asn-Val-Pro-Thr-Ile-Arg-Thr-Ala-Lys-Val-Gln | Poliovirus, VPg | 49 | 9 |
| K. | Gly-Ser-Gly-Val-Arg-Gly-Asp-Ser-Gly-Ser-Leu-Ala-Leu-Arg-Val-Ala-Arg-Gln-Leu-Pro | Foot and Mouth Disease VPI | 50 | 10 |
| L. | Arg-His-Lys-Gln-Lys-Ile-Val-Ala-Pro-Val-Lys-Gln-Thr-Leu | Foot and Mouth Disease VPI | 51 | 11 |
| M. | Gly-Leu-Phe-Gly-Ala-Ile-Ala-Gly-Phe-Ile-Glu | Influenza, HA2 Hemagglutinin protein | 52 | 12 |

The transformed bacteria of the invention are, in effect, therapeutic agents, and will be treated as such. They may be used alone or in association with pharmaceutically acceptable carriers of the type usually employed with such therapeutic agents. For oral or nasal administration, they may be suspended in aqueous isotonic saline which may be flavored or colored. For intestinal delivery, they may be placed in a capsule to deliver the transformed bacteria orally. Other methods of administration will be readily apparent to the skilled artisan and are within the scope of the invention.

Since the products of the invention are utilized as live transformed bacteria to colonize the selected site of administration, no specific dosage is required. Typically, the selected dosage form will contain from about $10^6$ to $10^{10}$ organisms per dosage unit.

REFERENCES

1. Fischetti. V. A., V. Pancholi and O. Schneewind. (1990) Mol. Microbiol. 4:1603.
2. Hollingshead, S. K., V. A. Fischetti, and J. R. Scott. 1986. J. Biol. Chem. 261:1677.
3. Miller, L., L. Gray, E. H. Beachey, and M. A. Kehoe. 1988 J. Biol. Chem. 263:5668.
4. Robbins, J. C., J. G. Spanier, S. J. Jones, W. J. Simpson, and P. P. Cleary. 1987. J. Bacteriol. 169:5633.
5. Mouw, A. R., E. H. Beachey and V. Burdett, 1988. J. Bacteriol. 170:676.
6. Haanes, E. J. and P. P. Cleary. 1989. J. Bacteriol. 171:6397.
7. Manjula, B. N., K. M. Khandke, T. Fairwell, W. A. Relf, and K. S. Sripakash. 1991. J. Protein Chem. 10:369.
8. Bessen, D. E. and V. A. Fischetti. 1992. Infect. Immun. 60:124.
9. Frithz, E., L-O. Heden, and G. Lindahl. 1989. Molec. Microbiol. 3:111.

10. Heath, D. G. and P. P. Cleary. 1989. Proc. Natl. Acad. Sci. U.S.A. 86:4741.
11. Gomi, H., T. Hozumi, S. Hattori, C. Tagawa, F. Kishimoto, and L. Bjorck. 1990. J. Immunol. 144:4046.
12. Chen, C. C. and P. P. Cleary. 1990. J. Biol. Chem. 265:3161.
13. Schneewind, O., K. F. Jones and V. A. Fischetti. 1990. J. Bacteriol. 172:3310.
14. Heden, L-O, E. Frithz, and G. Lindahl. 1991. Eur. J. Immunol.
15. Olsson, A., M. Eliasson, B. Guss, B. Nilsson, U. Hellman, M. Lindberg, and M. Uhlen. 1987. Eur. J. Biochem. 168:319.
16. Okahashi, N., C. Sasakawa, S. Yoshikawa, S. Hamada, and T. Koga. 1989. Molec. Microbiol. 3:673.
17. Kelly, C., P. Evans, L. Bergmeier, S.F. Lee, -Fox Progulske, A., A. C. Harris, A. Aitken, A. S. Bleiweis, and T. Lerner. 1990. FEBS Lett. 258:127.
18. Tokuda, M., N. Okahashi, I. Takahashi, M. Nakai. S. Nagaoka, M. Kawagoe, and T. Koga. 1991. Infec. Immun. 59:3309.
19. Ferretti, J. J., R. R. B. Russell, and M. L. Dao. 1989. Molec. Microbiol. 3:469.
20. Kao, S-M., S. B. Olmsted, A. S. Viksnins, J. C. Gallo, and G. M. Dunny. 1991. J. Bacteriol. 173:7650.
21. Galli, D., F. Lottspeich, and R. Wirth. 1990. Molec. Microbiol. 4:895.
22. Guss, B., M. Uhlen, B. Nilsson, M. Lindberg, J. Sjoquist, and J. Sjodahl. 1984. Eur. J. Biochem. 138:413.
23. Signas, C., G. Raucci, K. Jonsson, P. Lindgren, G. M. Anantharamaiah, M. Hook, and M. Lindberg. 1989. Proc. Natl. Acad. Sci. USA 86:699.
24. Kok, J., K. J. Leenhouts, A. J. Haandrikman, A. M. Ledeboer, and G. Venema. 1988. Appl. Environ. Microbiol. 54:231.
25. Gaillard, J. K., P. Berche, C. Frehel, E. Gouin, and P. Cossart. 1991. Cell 65:1.
26. Yeung, M. K. and J. O. Cisar. 1990. J. Bacteriol. 172:2462.
27. Yeung, M. K. and J. O. Cisar. 1988. J. Bacteriol. 170:3803.
28. Schneewind, O. V., Pancholi, and V. A. Fischetti. 1991. In: Genetics and Molecular Biology of Streptococci, Lactococci and Enterococci. G.M. Dunny, P. P. Cleary and L. L. McKay. ASM Publications, Washington. 152.
29. Pancholi, V. and V. A. Fischetti. 1988. J. Bacteriol. 170:2618–2624.
30. Maniatis, T., E. F. Fritsch and J. Sambrook. 1982. Molecular Cloning, Cold Spring Harbor Laboratory, Cold Spring Harbor.
31. Pozzi, G., R. A. Musmanno, P. M. Lievens, M. R. Oggioni, P. Plevani, and R. Manganelli. 1990. Res. Microbiol. 141:659–670.
32. Pozzi, G., R. A. Musmanno, M. Stellini, and A. M. Molina. 1987. FEMS Microbiol. Lett. 48:189.
33. Tommasino, M., M. Contorni, V. Scurlato, M. bugnoli, K. Maundell, and F. cavalieri. 1990. Gene 93:265.
34. Horinouchi, S. and B. Weisblum. 1982. J. Bacteriol. 150:804.
35. Hruby, Dennis F., V. M. Hodges, E. M. Wilson, C. A. Franke, and V. A. Fischetti. 1988. Proc. Natl. Acad. Scid. USA 85:5714.
36. Pozzi, G., W. R. Guild. 1985. J. Bacteriol. 161:909.
37. Hollingshead, S. K., V. A. Fischetti, and J. R. Scott. 1986. J. Biol. Chem. 261:1677–1686.
38. Wilson, C. R., S. E. Skinner, and W. V. Shaw. 1981. Plasmid 5:245–258.
39. Schwarz, E., U. K. Freese, L. Gissmann, W. Mayer, B. Roggenbuck, A. Stremlau, and H. zur Hausen. 1885. Nature 314:111–114.
40. Zavala, et al Science (1985) 228: 1436
41. McCutchan, et al Science (1985) 230: 1381
42. Udomsangpetch, et al Science (1986) 231: 57
43. Ravetch, et al Science (1984) 227: 1593
44. Neurath, et al Science (1984) 224: 392
45. Itoh, et al Proc. Natl. Acad. Sci. USA (1986) 83: 9174
46. Prince, et al Proc. Natl. Acad. Sci. USA (1982) 79: 579
47. Bhatnager, et al Proc. Natl. Acad. Sci. USA (1982) 79: 4400
48. Baron, et al Journal of Visology (1982) 43: 969
49. Baron, et al Cell (1982) 28: 395
50. Bittle, et al Nature (London) (1983) 298: 30
51. Atassi, et al Proc. Natl. Acad. Sci. USA (1982) 80: 840
52. Muller, et al Proc. Natl. Acad. Sci. USA (1982) 79: 569
53. Wang, et al Proc. Natl. Acad. Sci USA (1986) 83: 6159
54. O'Toole, P., L. Stenberg, M. Rissler, and G. Lindahl. 1992. Two major classes in the M protein family in group A streptococci. Proc. Natl. Acd. Sci. USA 89:8661.
55. Rakonjac, J. V., J. C. Robbins, and V. A. Fischetti. 1992. Cloning and sequencing of the gene encoding the serum opacity factor of *streptococcus pyogenes*: variation among different M types (Submitted).
56. Talay, R. S., P. Valentin-Weigand, P. G. Jerlstrom, K. N. Timmis, and G.S. Chhatwal. 1992. Fibronectin-binding protein of *Streptococcus pyogenes*: sequence of the binding domain involved in adherence of streptococci to epithelial cells. Infect. Immun. 60:3837.
57. Kastern, W., U. Sjobring, and L. bjorck. 1992. Structure of peptostreptococcal protein L and identification of a repeated immunoglobin light chain-binding domain J. Biol. Chem.
58. Michel, J. L., L. C. Madoff, K. Olson, D. E. Kling, D. L. Kasper, and F. M. Ausubel. 1992. Large, identical, tandem repeating units in the C protein alpha antigen gene, bca, of group B streptococci. Proc. Natl. Acad. Sci. USA 89:10060.
59. Lindgren, P-E., M. J. McGavin, and C. Signas. 1992. The nucleotide sequences of two different genes coding for fibronectin-binding proteins from *streptocuccus dysgalactiae* and identification of the binding domain. Molec. Microbiol.
60. Collins, C. M., A. Kimura, and A. L. Bisno. 1992. Group G streptococcal M protein exhibits structural features analogous to those of class I M protein of group A streptococci. Infect. Immun. 60:3689.
61. Sjobring, u. 1992. Isolation and molecular characterization for a novel albumin-binding protein from group G streptococci. Infect. Immun. 60:3601. 62. Smith, H. E., U. Vecht, A. L. J. Gielkens, and M. A. Smits. 1992. Cloning and nucleotide sequence of the. gene encoding the 136-kilodalton surface protein (muramidase-released protein) of *Streptococcus suis* type 2. Infect. Immun. 60:2361.
63. Jonsson, J., C. Signas, H-P. Muller, and M. Lindberg. 1991. Two different genes encode fibronectin binding proteins in *Staphylococcus aureus*. Eur. J. Biochem. 202:1041.
64. Patti, J. M., H. Jonsson, B. Guss, L. M. Switalski, K. Wiberg, M. Lindberg, and M. Hook. 1992. Molecular characterizations and expression of a gene encoding a *Staphylococcus aureus* collagen adhesin. J. Biol. Chem. 267:4766.
65. Schneewind, et al Cell (1992) 70:267
66. Fang, et al Proc. Natl. Acad. Sci. USA (1988) 85:895

Each of the publications cited is hereby incorporated by reference.

What is claimed is:

1. An isolated and purified DNA molecule encoding a hybrid protein, said hybrid protein comprising a heterologous polypeptide attached to the N-terminal end of the anchor region of a surface antigen of gram positive bacteria, wherein said DNA molecule, when expressed by gram positive bacteria, is expressed as a surface protein, with the anchor region bound to the bacteria and the heterologous peptide exposed on the surface of the bacteria.

2. A plasmid comprising the isolated and purified DNA molecule according to claim 1.

3. A chromosome comprising the isolated and purified DNA molecule according to claim 1.

4. The plasmid pVMB20, deposited at the American Type Culture Collection under the accession number PTA433.

5. The plasmid pVMB21.

6. The *S. gordonii* strain GP246.

7. An isolated and purified non-pathogenic gram positive bacteria which expresses a hybrid surface protein comprising an anchor sequence which is attached to the bacteria fused to a heterologous polypeptide, wherein said anchor sequence is the anchor sequence of a surface antigen of a gram positive bacteria.

8. The isolated and purified non-pathogenic gram-positive bacteria according to claim 7 wherein the heterologous polypeptide is an enzyme.

9. The isolated and purified non-pathogenic gram-positive bacteria according to claim 7 wherein the heterologous polypeptide is a surface antigen of a mammalian tumor cell.

10. The isolated and purified non-pathogenic gram-positive bacteria according to claim 7 wherein the heterologous polypeptide is a surface antigen of male sperm.

11. The isolated and purified gram-positive bacteria according to claim 7 wherein the heterologous polypeptide is an allergen.

12. The isolated and purified non-pathogenic gram-positive bacteria according to claim 7 wherein the heterologous polypeptide is selected from the group consisting of an antigenic determinant of a surface antigen of a bacteria, an antigenic determinant of a surface antigen of a virus, an antigenic determinant of a surface antigen of a parasite, and an antigenic determinant of a surface antigen of a fungus.

13. The isolated and purified gram-positive bacteria according to claim 7 wherein the anchor sequence is the anchor sequence of a streptococcal M protein.

14. The isolated and purified non-pathogenic gram-positive bacteria according to claim 13 wherein the heterologous polypeptide is selected from the group consisting of an antigenic determinant of a surface antigen of a bacteria, an antigenic determinant of a surface antigen of a virus, an antigenic determinant of a surface antigen of a parasite, and an antigenic determinant of a surface antigen of a fungus.

15. The isolated and purified non-pathogenic gram-positive bacteria of claim 7 wherein the hybrid surface protein is expressed by a plasmid.

16. The isolated and purified non-pathogenic gram-positive bacteria of claim 7 wherein the hybrid surface protein is expressed by a chromosomal gene.

17. *Streptococcus gordonii* which expresses the hybrid antigen M6:E7.

18. The *Streptococcus gordonii* according to claim 17, wherein said *S. gordonii* has been transformed with the plasmid pVMB21.

19. The *Streptococcus gordonii* according to claim 17, wherein said *S. gordonii* is *S. gordonii* strain GP246.

20. A pharmaceutical composition which comprises a pharmaceutically acceptable carrier and a non-pathogenic gram positive bacteria which expresses a hybrid surface protein, said protein being attached to the bacteria at the carboxy terminus of the anchor sequence of a surface antigen of a gram-positive bacteria, the balance of the hybrid surface protein being a heterologous polypeptide, wherein administration of said composition to a mammal results in the production of specific antibodies to said heteroloious polypeptide.

21. The composition according to claim 20 wherein the non-pathogenic gram-positive bacteria expressing a hybrid surface protein is streptococcus.

22. The composition according to claim 20 wherein the nonpathogenic gram-positive bacteria is *Streptococcus gordonii*.

23. The composition according to claim 22 wherein the nonpathogenic gram-positive bacteria is *Streptococcus gordonii* transformed to express the hybrid surface protein M6:E7.

24. The composition according to claim 23 wherein the *Streptococcus gordonii* is transformed by the plasmid pVMB21.

25. The composition according to claim 23 wherein the *Streptococcus gordonii* is *S. gordonii* strain GP246.

26. A method of producing antibodies to a polypeptide in animal in need of such treatment which comprises administration of the pharmaceutical composition according to claim 20 to said animal in an amount sufficient to produce antibodies against said polypeptide.

27. A composition of matter which comprises a carrier and a non-pathogenic gram positive bacteria which expresses a hybrid surface protein, said protein being attached to the bacteria at the carboxy terminus of the anchor sequence of a surface antigen of a gram-positive bacteria, the balance of the hybrid surface protein being a heterologous polypeptide which comprises the antigenic determinant of a surface antigen of a pathogenic bacteria.

28. The composition according to claim 27 wherein the antigenic determinant consists of the antigenic determinant of a surface antigen of a streptococcus.

29. The composition according to claim 27 wherein the nonpathogenic gram-positive bacteria is *Streptococcus gordonii*.

30. The composition according to claim 27 wherein the nonpathogenic gram-positive bacteria is *Streptococcus gordonii* transformed to express the hybrid surface protein M6:E7.

31. The composition according to claim 30 wherein the *Streptococcus gordonii* is transformed by the plasmid pVMB21.

32. The composition according to claim 30 wherein the *Streptococcus gordonii* is *S. gordonii* strain GP246.

33. A composition of matter comprising a non-pathogenic gram positive bacteria and a carrier therefor, wherein said bacteria expresses a hybrid surface protein, said hybrid surface protein being attached to the bacteria at the carboxy terminus of the anchor sequence of a surface antigen of a gram-positive bacteria, the balance of the hybrid surface protein being a heterologous polypeptide.

34. An isolated and purified DNA molecule encoding a hybrid protein, said hybrid protein comprising a heterologous polypeptide attached to the N-terminal end of the anchor region of a surface antigen of gram positive bacteria, wherein said anchor region comprises the amino acid sequence Leu-Pro-X-Thr-Gly-X, a hydrophobic domain, and a charged tail.

35. The isolated and purified DNA molecule according to claim 34, wherein said hydrophobic domain is from 15–20 amino acids long.

36. The isolated and purified DNA molecule according to claim 34, wherein said anchor region further comprises a spacer segment between the Leu-Pro-X-Thr-Gly-X sequence and the hydrophobic domain.

37. The isolated and purified DNA molecule according to claim 36, wherein said spacer segment is from 3 to 6 amino acids long.

38. The isolated and purified DNA molecule according to claim 34 wherein said charged tail is from 4 to 6 amino acids long.

39. The isolated and purified DNA molecule according to claim 34, wherein said anchor region consists of the amino acid sequence Leu-Pro-X-Thr-Gly-X, a spacer segment of 3–6 amino acids, a hydrophobic domain of 15–20 amino acids, and a charged tail of 4 to 6 amino acids.

40. The isolated and purified DNA molecule according to claim 34, wherein said anchor region consists of the amino acid sequence Leu-Pro-X-Thr-Gly-X, a spacer segment of 3 amino acids, a hydrophobic domain of 20 amino acids, and a charged tail of 6 amino acids.

41. The isolated and purified DNA molecule according to claim 40, wherein said anchor region consists of the amino acid sequence Leu-Pro-Ser-Thr-Gly-Glu-Thr-Ala-Asn-Pro-Phe-Phe-Thr-Ala-Ala-Ala-Leu-Thr-Val-Met-Ala-Thr-Ala-Gly-Val-Ala-Ala-Val-Val-Lys-Arg-Lys-Glu-Glu-Asn (SEQ ID NO: 1).

42. A plasmid comprising the isolated and purified DNA molecule according to claim 34.

43. A composition of matter comprising the isolated and purified DNA molecule according to claim 34 and a carrier therefor.

44. An isolated and purified microorganism transformed with the isolated and purified DNA molecule according to claim 34.

45. The isolated and purified microorganism according to claim 44 wherein said isolated and purified microorganism is a bacteria.

46. The isolated and purified microorganism according to claim 45 wherein said bacteria is gram-positive.

47. A composition of matter comprising the isolated and purified microorganism according to claim 44 and a carrier therefor.

* * * * *

SEQUENCE LISTING

<160> NUMBER OF SEQ ID NOS: 61

<210> SEQ ID NO 1
<211> LENGTH: 35
<212> TYPE: PRT
<213> ORGANISM: Streptococcus pyogenes

<400> SEQUENCE: 1

Leu Pro Ser Thr Gly Glu Thr Ala Asn Pro Phe Thr Ala Ala Ala
 1               5                  10                  15

Leu Thr Val Met Ala Thr Ala Gly Val Ala Ala Val Val Lys Arg Lys
            20                  25                  30

Glu Glu Asn
        35

<210> SEQ ID NO 2
<211> LENGTH: 20
<212> TYPE: PRT
<213> ORGANISM: Streptococcus pyogenes

<400> SEQUENCE: 2

Pro Phe Phe Thr Ala Ala Ala Leu Thr Val Met Ala Thr Ala Gly Val
 1               5                  10                  15

Ala Ala Val Val
            20

<210> SEQ ID NO 3
<211> LENGTH: 18
<212> TYPE: PRT
<213> ORGANISM: Plasmodium falciparum

<400> SEQUENCE: 3

Asn Ala Glu Asn Lys Glu Glu Leu Thr Ser Ser Asp Pro Glu Gly Gln
 1               5                  10                  15

Ile Met

<210> SEQ ID NO 4
<211> LENGTH: 28
<212> TYPE: PRT
<213> ORGANISM: Hepatitis, pre S(1)

<400> SEQUENCE: 4

Met Gln Trp Asn Ser Thr Ala Phe His Gln Thr Leu Gln Asp Pro Arg
 1               5                  10                  15

Val Arg Gly Leu Tyr Leu Tyr Leu Pro Ala Gly Gly
            20                  25

<210> SEQ ID NO 5
<211> LENGTH: 19
<212> TYPE: PRT
<213> ORGANISM: Hepatitis, pre S(2)

<400> SEQUENCE: 5

Asp Pro Arg Val Arg Gly Leu Tyr Phe Pro Ala Gly Gly Ser Ser Ser
 1               5                  10                  15

Gly Thr Val

<210> SEQ ID NO 6
<211> LENGTH: 11
<212> TYPE: PRT

```
<213> ORGANISM: Hepatitis Surface Antigen

<400> SEQUENCE: 6

Cys Thr Lys Pro Thr Asp Gly Asn Cys Thr Cys
 1               5                  10

<210> SEQ ID NO 7
<211> LENGTH: 12
<212> TYPE: PRT
<213> ORGANISM: Poliovirus, replicase protein

<400> SEQUENCE: 7

Tyr Ser Thr Leu Tyr Arg Trp Leu Asp Asp Ser Phe
 1               5                  10

<210> SEQ ID NO 8
<211> LENGTH: 13
<212> TYPE: PRT
<213> ORGANISM: Poliovirus, replicase protein

<400> SEQUENCE: 8

Asn Ala Pro Ser Lys Thr Lys Leu Glu Pro Ser Ala Phe
 1               5                  10

<210> SEQ ID NO 9
<211> LENGTH: 14
<212> TYPE: PRT
<213> ORGANISM: Poliovirus, VPg

<400> SEQUENCE: 9

Lys Lys Pro Asn Val Pro Thr Ile Arg Thr Ala Lys Val Gln
 1               5                  10

<210> SEQ ID NO 10
<211> LENGTH: 20
<212> TYPE: PRT
<213> ORGANISM: Foot-and-mouth disease virus

<400> SEQUENCE: 10

Gly Ser Gly Val Arg Gly Asp Ser Gly Ser Leu Ala Leu Arg Val Ala
 1               5                  10                  15

Arg Gln Leu Pro
            20

<210> SEQ ID NO 11
<211> LENGTH: 14
<212> TYPE: PRT
<213> ORGANISM: Foot-and-mouth disease virus

<400> SEQUENCE: 11

Arg His Lys Gln Lys Ile Val Ala Pro Val Lys Gln Thr Leu
 1               5                  10

<210> SEQ ID NO 12
<211> LENGTH: 11
<212> TYPE: PRT
<213> ORGANISM: Influenza, HA2

<400> SEQUENCE: 12

Gly Leu Phe Gly Ala Ile Ala Gly Phe Ile Glu
 1               5                  10

<210> SEQ ID NO 13
<211> LENGTH: 67
```

```
<212> TYPE: PRT
<213> ORGANISM: S. pyogenes

<400> SEQUENCE: 13

Pro Gly Asn Lys Val Val Pro Gly Lys Gly Gln Ala Pro Gln Ala Gly
 1               5                  10                  15

Thr Lys Pro Asn Gln Asn Lys Ala Pro Met Lys Glu Thr Lys Arg Gln
            20                  25                  30

Leu Pro Ser Thr Gly Glu Thr Ala Asn Pro Phe Phe Thr Ala Ala Ala
        35                  40                  45

Leu Thr Val Met Ala Thr Ala Gly Val Ala Val Val Lys Arg Lys
    50                  55                  60

Glu Glu Asn
 65

<210> SEQ ID NO 14
<211> LENGTH: 64
<212> TYPE: PRT
<213> ORGANISM: S. mutans

<400> SEQUENCE: 14

Gln Thr Lys Thr Thr Ala Ser Gln Thr Asn Val Pro Thr Thr Thr Asn
 1               5                  10                  15

Ile Thr Thr Ser Lys Gln Val Thr Lys Gln Lys Ala Lys Phe Val
            20                  25                  30

Leu Pro Ser Thr Gly Glu Gln Ala Gly Leu Leu Leu Thr Val Gly
        35                  40                  45

Leu Val Ile Val Ala Val Ala Gly Val Tyr Phe Tyr Arg Thr Arg Arg
    50                  55                  60

<210> SEQ ID NO 15
<211> LENGTH: 66
<212> TYPE: PRT
<213> ORGANISM: S. pyogenes

<400> SEQUENCE: 15

Glu Leu Ala Lys Leu Lys Gly Asn Gln Thr Pro Asn Ala Lys Val Ala
 1               5                  10                  15

Pro Gln Ala Asn Arg Ser Arg Ser Ala Met Thr Gln Gln Lys Arg Thr
            20                  25                  30

Leu Pro Ser Thr Gly Glu Thr Ala Asn Pro Pro Phe Thr Ala Ala Ala
        35                  40                  45

Ala Thr Val Met Val Ser Ala Gly Met Leu Ala Leu Lys Arg Lys Glu
    50                  55                  60

Glu Asn
 65

<210> SEQ ID NO 16
<211> LENGTH: 66
<212> TYPE: PRT
<213> ORGANISM: S. pyogenes

<400> SEQUENCE: 16

Glu Leu Ala Lys Leu Lys Gly Asn Gln Thr Pro Asn Ala Lys Val Ala
 1               5                  10                  15

Pro Gln Ala Asn Arg Ser Arg Ser Ala Met Thr Gln Gln Lys Arg Thr
            20                  25                  30

Leu Pro Ser Thr Gly Glu Thr Ala Asn Pro Phe Phe Thr Ala Ala Ala
        35                  40                  45
```

```
Ala Thr Val Met Val Ser Ala Gly Met Leu Ala Leu Lys Arg Lys Glu
         50                  55                  60

Glu Asn
 65

<210> SEQ ID NO 17
<211> LENGTH: 47
<212> TYPE: PRT
<213> ORGANISM: S. pyogenes

<400> SEQUENCE: 17

Pro Asp Thr Lys Pro Gly Asn Lys Glu Val Pro Thr Arg Pro Ser Gln
  1               5                  10                  15

Thr Arg Thr Asn Thr Asn Lys Ala Pro Met Ala Gln Thr Lys Arg Gln
             20                  25                  30

Leu Pro Ser Thr Gly Glu Glu Thr Thr Asn Pro Phe Phe Thr Ala
         35                  40                  45

<210> SEQ ID NO 18
<211> LENGTH: 67
<212> TYPE: PRT
<213> ORGANISM: S. aureus

<400> SEQUENCE: 18

Lys Leu Ala Asp Lys Asn Met Ile Lys Pro Gly Gln Glu Leu Val Val
  1               5                  10                  15

Asp Lys Lys Gln Pro Ala Asn His Ala Asp Ala Asn Lys Ala Gln Ala
             20                  25                  30

Leu Pro Glu Thr Gly Val Glu Asn Pro Leu Ile Gly Thr Thr Val Phe
         35                  40                  45

Gly Gly Leu Ser Leu Ala Leu Gly Ala Ala Leu Leu Ala Gly Arg Arg
     50                  55                  60

Arg Glu Leu
 65

<210> SEQ ID NO 19
<211> LENGTH: 66
<212> TYPE: PRT
<213> ORGANISM: Gr. G strep

<400> SEQUENCE: 19

Pro Ile Ala Lys Asp Asp Ala Lys Lys Asp Thr Lys Lys Glu Asp Ala
  1               5                  10                  15

Ala Lys Lys Pro Glu Ala Lys Lys Asp Asp Ala Lys Lys Ala Glu Thr
             20                  25                  30

Leu Pro Thr Thr Gly Glu Gly Asn Pro Phe Phe Thr Ala Ala Ala Leu
         35                  40                  45

Ala Val Met Ala Gly Ala Gly Ala Leu Ala Val Ala Gly Lys Arg Lys
     50                  55                  60

Glu Asp
 65

<210> SEQ ID NO 20
<211> LENGTH: 69
<212> TYPE: PRT
<213> ORGANISM: S. aureus

<400> SEQUENCE: 20

Val Glu Gln Gly Lys Val Val Thr Pro Val Ile Glu Ile Asn Glu Lys
```

-continued

```
                1               5                  10                    15
        Val Lys Ala Val Ala Pro Thr Lys Lys Pro Gln Ser Lys Lys Ser Glu
                        20                  25                  30

Leu Pro Glu Thr Gly Gly Glu Glu Ser Thr Asn Lys Gly Met Leu Phe
                    35                  40                  45

Gly Gly Leu Phe Ser Ile Leu Gly Leu Ala Leu Leu Arg Arg Asn Lys
                50                  55                  60

Lys Asn His Lys Ala
        65

<210> SEQ ID NO 21
<211> LENGTH: 66
<212> TYPE: PRT
<213> ORGANISM: S. pyogenes

<400> SEQUENCE: 21

Lys Ala Leu Thr Asp Gly Thr Thr Phe Ser Lys Ser Asn Glu Gly Ser
        1               5                  10                    15

Gly Thr Val Leu Leu Glu Thr Asp Ile Pro Asn Thr Lys Leu Gly Glu
                        20                  25                  30

Leu Pro Ser Thr Gly Ser Ile Gly Thr Tyr Leu Phe Lys Ala Ile Gly
                    35                  40                  45

Ser Ala Ala Met Ile Gly Ala Ile Gly Ile Tyr Ile Val Lys Arg Arg
                50                  55                  60

Lys Ala
        65

<210> SEQ ID NO 22
<211> LENGTH: 66
<212> TYPE: PRT
<213> ORGANISM: S. mutans

<400> SEQUENCE: 22

Thr Asp Pro Gln Asp Pro Ser Ser Pro Arg Thr Ser Thr Val Ile Ile
        1               5                  10                    15

Tyr Lys Pro Gln Ser Thr Ala Tyr Gln Pro Ser Ser Val Gln Glu Thr
                        20                  25                  30

Leu Pro Asn Thr Gly Val Thr Asn Asn Ala Tyr Met Pro Leu Leu Gly
                    35                  40                  45

Ile Ile Gly Leu Val Thr Ser Phe Ser Leu Leu Gly Leu Lys Ala Lys
                50                  55                  60

Lys Asp
        65

<210> SEQ ID NO 23
<211> LENGTH: 68
<212> TYPE: PRT
<213> ORGANISM: S. cremoris

<400> SEQUENCE: 23

Gly Gly Asn Ile Pro Thr Asn Pro Ala Thr Thr Thr Ser Thr Ser Thr
        1               5                  10                    15

Asp Asp Thr Thr Asp Arg Asn Gly Gln Leu Thr Ser Gly Lys Gly Ala
                        20                  25                  30

Leu Pro Lys Thr Gly Glu Thr Thr Glu Arg Pro Ala Phe Gly Phe Leu
                    35                  40                  45

Gly Val Ile Val Val Ile Leu Met Gly Val Leu Gly Leu Lys Arg Lys
                50                  55                  60
```

-continued

Gln Arg Glu Glu
 65

<210> SEQ ID NO 24
<211> LENGTH: 66
<212> TYPE: DNA
<213> ORGANISM: S. pyogenes

<400> SEQUENCE: 24
ccaatgaagg aaactaagag acagttacca tcaacaggtg aaacagctaa cccattcttc    60
acagcg                                                              66

<210> SEQ ID NO 25
<211> LENGTH: 28
<212> TYPE: DNA
<213> ORGANISM: S. mutans

<400> SEQUENCE: 25
acacaaggat tgttcaagg gttgatat                                       28

<210> SEQ ID NO 26
<211> LENGTH: 18
<212> TYPE: DNA
<213> ORGANISM: S. pyogenes

<400> SEQUENCE: 26
aatagtggat cagcgcta                                                 18

<210> SEQ ID NO 27
<211> LENGTH: 12
<212> TYPE: DNA
<213> ORGANISM: S. pyogenes

<400> SEQUENCE: 27
gcaccaacgc ta                                                       12

<210> SEQ ID NO 28
<211> LENGTH: 24
<212> TYPE: DNA
<213> ORGANISM: S. pyogenes

<400> SEQUENCE: 28
tgccaagcga acaacccat tcat                                           24

<210> SEQ ID NO 29
<211> LENGTH: 39
<212> TYPE: DNA
<213> ORGANISM: S. aureus

<400> SEQUENCE: 29
ggatggtaca agctcagcag atcgaaacca ttcaggtat                          39

<210> SEQ ID NO 30
<211> LENGTH: 31
<212> TYPE: DNA
<213> ORGANISM: Gr. G strep

<400> SEQUENCE: 30
gagacgctag aagctgaact cttatggagc a                                  31

<210> SEQ ID NO 31
<211> LENGTH: 41

```
<212> TYPE: DNA
<213> ORGANISM: S. aureus

<400> SEQUENCE: 31
aaccacatct agatctgact gaggaaatca aaaaaggta t                           41

<210> SEQ ID NO 32
<211> LENGTH: 36
<212> TYPE: DNA
<213> ORGANISM: S. pyogenes

<400> SEQUENCE: 32
atccctcacc agctagtgat gagcttgctt acctat                               36

<210> SEQ ID NO 33
<211> LENGTH: 40
<212> TYPE: DNA
<213> ORGANISM: S. mutans

<400> SEQUENCE: 33
agccagctct gtcagaacaa atgataactg tatagcttta                           40

<210> SEQ ID NO 34
<211> LENGTH: 36
<212> TYPE: DNA
<213> ORGANISM: S. cremoris

<400> SEQUENCE: 34
actcatccgg ggcacaagag agggccagc gtttgc                                36

<210> SEQ ID NO 35
<211> LENGTH: 440
<212> TYPE: PRT
<213> ORGANISM: S. pyogenes

<400> SEQUENCE: 35
```

Arg Val Phe Pro Arg Gly Thr Val Glu Asn Pro Asp Lys Ala Arg Glu
 1               5                  10                  15

Leu Leu Asn Lys Tyr Asp Val Glu Asn Ser Met Leu Gln Ala Asn Asn
             20                  25                  30

Asp Lys Leu Thr Thr Glu Asn Asn Leu Thr Asp Gln Asn Lys Asn
         35                  40                  45

Leu Thr Thr Glu Asn Lys Asn Leu Thr Asp Gln Asn Lys Asn Leu Thr
     50                  55                  60

Thr Glu Asn Lys Asn Leu Thr Asp Gln Asn Lys Asn Leu Thr Thr Glu
 65                  70                  75                  80

Asn Lys Glu Leu Lys Ala Glu Gly Asn Arg Leu Thr Thr Glu Asn Lys
                 85                  90                  95

Gly Leu Thr Lys Lys Leu Ser Glu Ala Glu Glu Ala Ala Asn Lys
            100                 105                 110

Glu Arg Glu Asn Lys Glu Ala Ile Gly Thr Leu Lys Lys Thr Leu Asp
        115                 120                 125

Glu Thr Val Lys Asp Lys Ile Ala Lys Glu Gln Glu Ser Lys Glu Thr
    130                 135                 140

Ile Gly Thr Leu Lys Lys Thr Leu Asp Glu Thr Val Lys Asp Lys Ile
145                 150                 155                 160

Ala Lys Glu Gln Glu Ser Lys Glu Thr Ile Gly Thr Leu Lys Lys Thr
                165                 170                 175

Leu Asp Glu Thr Val Lys Asp Lys Ile Ala Lys Glu Gln Glu Ser Lys

```
                 180                 185                 190
Glu Thr Ile Gly Thr Leu Lys Lys Ile Leu Asp Glu Thr Val Lys Asp
             195                 200                 205
Lys Ile Ala Arg Glu Gln Lys Ser Lys Gln Asp Ile Gly Ala Leu Lys
         210                 215                 220
Gln Glu Leu Ala Lys Lys Asp Glu Gly Asn Lys Val Ser Glu Ala Ser
225                 230                 235                 240
Arg Lys Gly Leu Arg Arg Asp Leu Asp Ala Ser Arg Glu Ala Lys Lys
                 245                 250                 255
Gln Val Glu Lys Asp Leu Ala Asn Leu Thr Ala Glu Leu Asp Lys Val
             260                 265                 270
Lys Glu Glu Lys Gln Ile Ser Asp Ala Ser Arg Gln Gly Leu Arg Arg
         275                 280                 285
Asp Leu Asp Ala Ser Arg Glu Ala Lys Lys Gln Val Glu Lys Ala Leu
     290                 295                 300
Glu Glu Ala Asn Ser Lys Leu Ala Ala Leu Glu Lys Leu Asn Lys Glu
305                 310                 315                 320
Leu Glu Glu Ser Lys Lys Leu Thr Glu Lys Glu Lys Ala Glu Leu Gln
                 325                 330                 335
Ala Lys Leu Glu Ala Glu Ala Lys Ala Leu Lys Glu Gln Leu Ala Lys
             340                 345                 350
Gln Ala Glu Glu Leu Ala Lys Leu Arg Ala Gly Lys Ala Ser Asp Ser
         355                 360                 365
Gln Thr Pro Asp Ala Lys Pro Gly Asn Lys Val Val Pro Gly Lys Gly
     370                 375                 380
Gln Ala Pro Glu Ala Gly Thr Lys Pro Asn Gln Asn Lys Ala Pro Met
385                 390                 395                 400
Lys Glu Thr Lys Arg Gln Leu Pro Ser Thr Gly Glu Thr Ala Asn Pro
                 405                 410                 415
Phe Phe Thr Ala Ala Ala Leu Thr Val Met Ala Thr Ala Gly Val Ala
             420                 425                 430
Ala Val Lys Arg Lys Glu Glu Asn
         435                 440

<210> SEQ ID NO 36
<211> LENGTH: 6
<212> TYPE: PRT
<213> ORGANISM: S. pyogenes

<400> SEQUENCE: 36

Leu Pro Ser Thr Gly Glu
 1               5

<210> SEQ ID NO 37
<211> LENGTH: 6
<212> TYPE: PRT
<213> ORGANISM: S. pyogenes
<220> FEATURE:
<221> NAME/KEY: PEPTIDE
<222> LOCATION: (3)..(6)
<223> OTHER INFORMATION: Amino acids 3 and 6 are Xaa wherein Xaa = any
      amino acid.

<400> SEQUENCE: 37

Leu Pro Xaa Thr Gly Xaa
 1               5

<210> SEQ ID NO 38
```

```
<211> LENGTH: 6
<212> TYPE: PRT
<213> ORGANISM: S. pyogenes

<400> SEQUENCE: 38

Leu Pro Thr Thr Asn Asp
 1               5

<210> SEQ ID NO 39
<211> LENGTH: 6
<212> TYPE: PRT
<213> ORGANISM: S. pyogenes

<400> SEQUENCE: 39

Leu Pro Ser Thr Gly Ser
 1               5

<210> SEQ ID NO 40
<211> LENGTH: 6
<212> TYPE: PRT
<213> ORGANISM: Gr. B strep

<400> SEQUENCE: 40

Leu Pro Tyr Thr Gly Val
 1               5

<210> SEQ ID NO 41
<211> LENGTH: 6
<212> TYPE: PRT
<213> ORGANISM: Gr. B strep

<400> SEQUENCE: 41

Leu Pro Thr Thr Gly Glu
 1               5

<210> SEQ ID NO 42
<211> LENGTH: 6
<212> TYPE: PRT
<213> ORGANISM: S. mutans

<400> SEQUENCE: 42

Leu Pro Asn Thr Gly Glu
 1               5

<210> SEQ ID NO 43
<211> LENGTH: 6
<212> TYPE: PRT
<213> ORGANISM: S. sobrinus

<400> SEQUENCE: 43

Leu Pro Ala Thr Gly Asp
 1               5

<210> SEQ ID NO 44
<211> LENGTH: 6
<212> TYPE: PRT
<213> ORGANISM: E. fecalis

<400> SEQUENCE: 44

Leu Pro Gln Thr Gly Glu
 1               5

<210> SEQ ID NO 45
<211> LENGTH: 6
<212> TYPE: PRT
```

<213> ORGANISM: S. aureus

<400> SEQUENCE: 45

Leu Pro Glu Thr Gly Val
 1               5

<210> SEQ ID NO 46
<211> LENGTH: 6
<212> TYPE: PRT
<213> ORGANISM: S. aureus

<400> SEQUENCE: 46

Leu Pro Glu Thr Gly Gly
 1               5

<210> SEQ ID NO 47
<211> LENGTH: 6
<212> TYPE: PRT
<213> ORGANISM: L. monocytogenes

<400> SEQUENCE: 47

Leu Pro Thr Thr Gly Glu
 1               5

<210> SEQ ID NO 48
<211> LENGTH: 6
<212> TYPE: PRT
<213> ORGANISM: A. viscosis

<400> SEQUENCE: 48

Leu Pro Leu Thr Gly Ala
 1               5

<210> SEQ ID NO 49
<211> LENGTH: 6
<212> TYPE: PRT
<213> ORGANISM: S. pyogenes

<400> SEQUENCE: 49

Leu Pro Ala Ser Gly Asp
 1               5

<210> SEQ ID NO 50
<211> LENGTH: 6
<212> TYPE: PRT
<213> ORGANISM: P. magnus

<400> SEQUENCE: 50

Leu Pro Lys Ala Gly Ser
 1               5

<210> SEQ ID NO 51
<211> LENGTH: 6
<212> TYPE: PRT
<213> ORGANISM: Gr. B strep

<400> SEQUENCE: 51

Leu Pro Ala Thr Gly Glu
 1               5

<210> SEQ ID NO 52
<211> LENGTH: 6
<212> TYPE: PRT
<213> ORGANISM: S. dysgalactiae

```
<400> SEQUENCE: 52

Leu Pro Gln Thr Gly Thr

<210> SEQ ID NO 53
<211> LENGTH: 6
<212> TYPE: PRT
<213> ORGANISM: S. dysgalactiae

<400> SEQUENCE: 53

Leu Pro Ala Ala Gly Glu
 1               5

<210> SEQ ID NO 54
<211> LENGTH: 6
<212> TYPE: PRT
<213> ORGANISM: S. aureus

<400> SEQUENCE: 54

Leu Pro Glu Thr Gly Gly
 1               5

<210> SEQ ID NO 55
<211> LENGTH: 6
<212> TYPE: PRT
<213> ORGANISM: S. aureus

<400> SEQUENCE: 55

Leu Pro Lys Thr Gly Met
 1               5

<210> SEQ ID NO 56
<211> LENGTH: 4
<212> TYPE: PRT
<213> ORGANISM: plasmodium falciparum

<400> SEQUENCE: 56

Asn Ala Asn Pro

<210> SEQ ID NO 57
<211> LENGTH: 9
<212> TYPE: PRT
<213> ORGANISM: plasmodium vivax

<400> SEQUENCE: 57

Gly Asp Arg Ala Asp Gly Gln Pro Ala
 1               5

<210> SEQ ID NO 58
<211> LENGTH: 8
<212> TYPE: PRT
<213> ORGANISM: plasmodium falciparum

<400> SEQUENCE: 58

Glu Gln Asn Val Glu His Asp Ala
 1               5

<210> SEQ ID NO 59
<211> LENGTH: 6
<212> TYPE: PRT
<213> ORGANISM: E. fecalis

<400> SEQUENCE: 59

Leu Pro Lys Thr Gly Glu
 1               5
```

```
<210> SEQ ID NO 60
<211> LENGTH: 3
<212> TYPE: PRT
<213> ORGANISM: Artificial Sequence
<220> FEATURE:
<223> OTHER INFORMATION: spacer segment residues

<400> SEQUENCE: 60

Thr Ala Asn
 1

<210> SEQ ID NO 61
<211> LENGTH: 6
<212> TYPE: PRT
<213> ORGANISM: Artificial Sequence
<220> FEATURE:
<223> OTHER INFORMATION: highly charged tail segment residues

<400> SEQUENCE: 61

Lys Arg Lys Glu Glu Asn
 1               5
```